(12) United States Patent
Weber et al.

(10) Patent No.: US 8,133,199 B2
(45) Date of Patent: Mar. 13, 2012

(54) ELECTROACTIVE POLYMER ACTIVATION SYSTEM FOR A MEDICAL DEVICE

(75) Inventors: Jan Weber, Maastricht (NL); Kent D. Harrison, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 299 days.

(21) Appl. No.: 12/199,720

(22) Filed: Aug. 27, 2008

(65) Prior Publication Data

US 2010/0056985 A1 Mar. 4, 2010

(51) Int. Cl.
*A61M 29/00* (2006.01)
*A61M 31/00* (2006.01)

(52) U.S. Cl. ............... 604/97.03; 604/509; 604/96.01; 604/508; 604/97.01; 604/99.01; 604/100.01

(58) Field of Classification Search ............ 623/1.11; 604/96.01, 97.01–97.03, 99.01, 100.01, 101.01–101.05, 604/102.01–102.02, 103.01–103.02; 606/108
See application file for complete search history.

(56) References Cited

U.S. PATENT DOCUMENTS

| | | | |
|---|---|---|---|
| 4,273,111 A | 6/1981 | Tsukaya |
| 4,286,585 A | 9/1981 | Ogawa |
| 4,448,195 A | 5/1984 | LeVeen et al. |
| 4,484,585 A | 11/1984 | Baier |
| 4,499,895 A | 2/1985 | Takayama |
| 4,503,842 A | 3/1985 | Takayama |
| 4,543,090 A | 9/1985 | McCoy |
| 4,601,701 A | 7/1986 | Mueller, Jr. |
| 4,601,705 A | 7/1986 | McCoy |
| 4,753,223 A | 6/1988 | Bremer |
| 4,769,005 A | 9/1988 | Ginsburg et al. |
| 4,776,337 A | 10/1988 | Palmaz |
| 4,790,624 A | 12/1988 | Van Hoye et al. |
| 4,793,359 A | 12/1988 | Sharrow |
| 4,830,023 A | 5/1989 | De Toledo et al. |
| 4,838,859 A | 6/1989 | Strassmann |
| 4,846,573 A | 7/1989 | Taylor et al. |

(Continued)

FOREIGN PATENT DOCUMENTS

CA 2517380 9/2004

(Continued)

OTHER PUBLICATIONS

"Medical Urethanes Overview," Noveon, the Specialty Chemicals Innovator, 11 pages, prior to Jan. 13, 2004.

(Continued)

*Primary Examiner* — Kevin C Sirmons
*Assistant Examiner* — Bradley Thomas, Jr.
(74) *Attorney, Agent, or Firm* — Seager, Tufte & Wickhem, LLC

(57) ABSTRACT

An activation circuit for selectively providing an electrical current to one or more electroactive polymers (EAPs) in a medical device is disclosed. The activation circuit may include a sensor for sensing a measure related to a parameter of an elongated member and/or a balloon of the medical device. The electrical current may be provided to the one or more EAPs according to the sensed parameter of the elongated member and/or the balloon of the medical device. In some cases, the activation circuit may include a comparator for comparing the sensed measure to a threshold to determine when the electrical current is applied to the EAPs. The parameter may be a pressure, a fluid flow, a temperature, and/or other suitable parameter.

22 Claims, 9 Drawing Sheets

U.S. PATENT DOCUMENTS

| | | | |
|---|---|---|---|
| 4,884,557 A | 12/1989 | Takehana et al. | |
| 4,899,731 A | 2/1990 | Takayama et al. | |
| 4,906,244 A | 3/1990 | Pinchuk et al. | |
| 4,913,141 A | 4/1990 | Hillstead | |
| 4,930,494 A | 6/1990 | Takehana et al. | |
| 4,950,239 A | 8/1990 | Gahara et al. | |
| 4,977,886 A | 12/1990 | Takehana et al. | |
| 4,987,314 A | 1/1991 | Gotanda et al. | |
| 4,988,356 A | 1/1991 | Crittenden et al. | |
| 4,994,071 A | 2/1991 | MacGregor | |
| 4,998,923 A | 3/1991 | Samson et al. | |
| 5,019,085 A | 5/1991 | Hillstead et al. | |
| 5,090,956 A | 2/1992 | McCoy | |
| 5,100,933 A | 3/1992 | Tanaka et al. | |
| 5,120,308 A | 6/1992 | Hess | |
| 5,122,154 A | 6/1992 | Rhodes | |
| 5,188,111 A | 2/1993 | Yates et al. | |
| 5,195,984 A | 3/1993 | Schatz | |
| 5,209,728 A | 5/1993 | Kraus et al. | |
| 5,219,335 A | 6/1993 | Willard et al. | |
| 5,219,355 A | 6/1993 | Parodi et al. | |
| 5,239,982 A | 8/1993 | Trauthen | |
| 5,246,421 A | 9/1993 | Saab | |
| 5,250,167 A | 10/1993 | Adolf et al. | |
| 5,257,974 A | 11/1993 | Cox | |
| 5,268,082 A | 12/1993 | Oguro et al. | |
| 5,286,259 A * | 2/1994 | Ganguly et al. | 604/96.01 |
| 5,290,306 A | 3/1994 | Trotta et al. | |
| 5,316,023 A | 5/1994 | Palmaz et al. | |
| 5,318,535 A | 6/1994 | Miraki | |
| 5,324,259 A | 6/1994 | Taylor et al. | |
| 5,337,732 A | 8/1994 | Grundfest et al. | |
| 5,347,987 A | 9/1994 | Feldstein et al. | |
| 5,348,537 A | 9/1994 | Wiesner et al. | |
| 5,368,015 A | 11/1994 | Wilk | |
| 5,380,299 A | 1/1995 | Fearnot et al. | |
| 5,389,222 A | 2/1995 | Shahinpoor | |
| 5,396,879 A | 3/1995 | Wilk et al. | |
| 5,397,305 A | 3/1995 | Kawula et al. | |
| 5,409,458 A | 4/1995 | Khairkhahan et al. | |
| 5,425,703 A | 6/1995 | Feiring | |
| 5,431,645 A | 7/1995 | Smith et al. | |
| 5,449,343 A | 9/1995 | Samson et al. | |
| 5,449,353 A | 9/1995 | Watanabe et al. | |
| 5,449,382 A | 9/1995 | Dayton | |
| 5,477,856 A | 12/1995 | Lundquist | |
| 5,482,029 A | 1/1996 | Sekiguchi et al. | |
| 5,492,121 A | 2/1996 | Lu | |
| 5,492,532 A | 2/1996 | Ryan et al. | |
| 5,500,181 A | 3/1996 | Wang et al. | |
| 5,556,370 A | 9/1996 | Maynard | |
| 5,556,413 A | 9/1996 | Lam | |
| 5,556,700 A | 9/1996 | Kaneto et al. | |
| 5,571,086 A | 11/1996 | Kaplan et al. | |
| 5,609,627 A | 3/1997 | Goicoechea et al. | |
| 5,613,980 A | 3/1997 | Chauhan | |
| 5,624,380 A | 4/1997 | Takayama et al. | |
| 5,631,040 A | 5/1997 | Takuchi et al. | |
| 5,632,763 A | 5/1997 | Glastra | |
| 5,643,278 A | 7/1997 | Wijay | |
| 5,645,520 A | 7/1997 | Nakamura et al. | |
| 5,649,923 A | 7/1997 | Gregory et al. | |
| 5,651,366 A | 7/1997 | Liang et al. | |
| 5,662,587 A | 9/1997 | Grundfest et al. | |
| 5,670,161 A | 9/1997 | Healy et al. | |
| 5,683,345 A | 11/1997 | Waksman et al. | |
| 5,693,015 A | 12/1997 | Walker et al. | |
| 5,697,948 A | 12/1997 | Marin et al. | |
| 5,697,971 A | 12/1997 | Fischell et al. | |
| 5,720,735 A | 2/1998 | Dorros | |
| 5,725,519 A | 3/1998 | Penner et al. | |
| 5,744,515 A | 4/1998 | Clapper | |
| 5,749,825 A | 5/1998 | Fischell et al. | |
| 5,755,734 A | 5/1998 | Richter et al. | |
| 5,755,735 A | 5/1998 | Richter et al. | |
| 5,755,778 A | 5/1998 | Kleshinski | |
| 5,766,013 A | 6/1998 | Vuyk | |
| 5,771,902 A | 6/1998 | Lee et al. | |
| 5,772,628 A | 6/1998 | Nguyen et al. | |
| 5,772,669 A | 6/1998 | Vrba | |
| 5,776,141 A | 7/1998 | Klein et al. | |
| 5,792,100 A * | 8/1998 | Shantha | 604/509 |
| 5,797,952 A | 8/1998 | Klein | |
| 5,817,100 A | 10/1998 | Igaki | |
| 5,824,055 A | 10/1998 | Spiridigliozzi et al. | |
| 5,836,952 A | 11/1998 | Davis et al. | |
| 5,843,027 A | 12/1998 | Stone et al. | |
| 5,855,565 A | 1/1999 | Bar-Cohen et al. | |
| 5,857,962 A | 1/1999 | Bracci et al. | |
| 5,873,817 A | 2/1999 | Kokish et al. | |
| 5,873,906 A | 2/1999 | Lau et al. | |
| 5,876,374 A | 3/1999 | Alba et al. | |
| 5,893,868 A | 4/1999 | Hanson et al. | |
| 5,906,591 A | 5/1999 | Dario et al. | |
| 5,906,640 A | 5/1999 | Penn et al. | |
| 5,908,405 A | 6/1999 | Imran et al. | |
| 5,916,146 A | 6/1999 | Allotta et al. | |
| 5,916,263 A | 6/1999 | Goicoechea et al. | |
| 5,921,995 A | 7/1999 | Kleshinski | |
| 5,935,161 A | 8/1999 | Robinson et al. | |
| 5,941,908 A | 8/1999 | Goldsteen et al. | |
| 5,951,569 A | 9/1999 | Tuckey et al. | |
| 5,957,833 A | 9/1999 | Shan | |
| 5,957,929 A | 9/1999 | Brenneman | |
| 5,961,546 A | 10/1999 | Robinson et al. | |
| 5,961,548 A | 10/1999 | Shmulewitz | |
| 5,968,068 A | 10/1999 | Dehdashtian et al. | |
| 6,010,449 A | 1/2000 | Selmon et al. | |
| 6,013,092 A | 1/2000 | Dehdashtian et al. | |
| 6,015,424 A | 1/2000 | Rosenbluth et al. | |
| 6,017,324 A | 1/2000 | Tu et al. | |
| 6,017,362 A | 1/2000 | Lau | |
| 6,027,460 A | 2/2000 | Shturman | |
| 6,033,434 A | 3/2000 | Borghi | |
| 6,048,350 A | 4/2000 | Vrba | |
| 6,048,361 A | 4/2000 | Von Oepen | |
| 6,056,722 A | 5/2000 | Jayaraman | |
| 6,056,775 A | 5/2000 | Borghi et al. | |
| 6,059,813 A | 5/2000 | Vrba et al. | |
| 6,071,234 A | 6/2000 | Takada | |
| 6,071,285 A | 6/2000 | Lashinski et al. | |
| 6,071,286 A | 6/2000 | Mawad | |
| 6,077,297 A | 6/2000 | Robinson et al. | |
| 6,090,127 A | 7/2000 | Globerman | |
| 6,096,073 A | 8/2000 | Webster et al. | |
| 6,099,497 A | 8/2000 | Adams et al. | |
| 6,109,852 A | 8/2000 | Shahinpoor et al. | |
| 6,110,191 A | 8/2000 | Dehdashtian et al. | |
| 6,117,117 A | 9/2000 | Mauch | |
| 6,117,156 A | 9/2000 | Richter et al. | |
| 6,117,296 A | 9/2000 | Thomson | |
| 6,120,522 A | 9/2000 | Vrba et al. | |
| 6,129,738 A | 10/2000 | Lashinski et al. | |
| 6,132,450 A | 10/2000 | Hanson et al. | |
| 6,139,510 A | 10/2000 | Palermo | |
| 6,142,973 A | 11/2000 | Carleton et al. | |
| 6,143,014 A | 11/2000 | Dehdashtian et al. | |
| 6,146,415 A | 11/2000 | Fitz | |
| 6,152,944 A | 11/2000 | Holman et al. | |
| 6,162,171 A | 12/2000 | Ng et al. | |
| 6,165,195 A | 12/2000 | Wilson et al. | |
| 6,165,196 A | 12/2000 | Stack et al. | |
| 6,165,210 A | 12/2000 | Lau et al. | |
| 6,187,015 B1 | 2/2001 | Brenneman | |
| 6,190,354 B1 * | 2/2001 | Sell et al. | 604/96.01 |
| 6,190,360 B1 | 2/2001 | Iancea et al. | |
| 6,190,393 B1 | 2/2001 | Bevier et al. | |
| 6,203,568 B1 | 3/2001 | Lombardi et al. | |
| 6,210,380 B1 | 4/2001 | Mauch | |
| 6,210,429 B1 | 4/2001 | Vardi et al. | |
| 6,210,431 B1 | 4/2001 | Power | |
| 6,221,090 B1 | 4/2001 | Wilson | |
| 6,221,097 B1 | 4/2001 | Wang et al. | |
| 6,224,587 B1 | 5/2001 | Gibson | |
| 6,238,410 B1 | 5/2001 | Vrba et al. | |
| 6,246,914 B1 | 6/2001 | De la Rama et al. | |
| 6,249,076 B1 | 6/2001 | Madden et al. | |

| | | |
|---|---|---|
| 6,254,593 B1 | 7/2001 | Wilson |
| 6,258,052 B1 | 7/2001 | Milo |
| 6,258,073 B1 | 7/2001 | Mauch |
| 6,261,316 B1 | 7/2001 | Shaolian et al. |
| 6,264,682 B1 | 7/2001 | Wilson et al. |
| 6,264,688 B1 | 7/2001 | Herklotz et al. |
| 6,280,466 B1 | 8/2001 | Kugler et al. |
| 6,287,277 B1 | 9/2001 | Yan |
| 6,287,330 B1 | 9/2001 | Johansson et al. |
| 6,290,668 B1 | 9/2001 | Gregory et al. |
| 6,290,673 B1 | 9/2001 | Shanley |
| 6,299,636 B1 | 10/2001 | Schmitt et al. |
| 6,302,906 B1 | 10/2001 | Goicoechea et al. |
| 6,315,790 B1 | 11/2001 | Gerberding et al. |
| 6,319,275 B1 | 11/2001 | Lashinski et al. |
| 6,322,548 B1 | 11/2001 | Payne et al. |
| 6,346,089 B1 | 2/2002 | Dibie |
| 6,350,278 B1 | 2/2002 | Lenker et al. |
| 6,352,561 B1 | 3/2002 | Leopold et al. |
| 6,361,544 B1 | 3/2002 | Wilson et al. |
| 6,361,555 B1 | 3/2002 | Wilson |
| 6,364,893 B1 | 4/2002 | Sahatjian et al. |
| 6,371,978 B1 | 4/2002 | Wilson |
| 6,375,660 B1 | 4/2002 | Fischell et al. |
| 6,375,675 B2 | 4/2002 | Dehdashtian et al. |
| 6,379,372 B1 | 4/2002 | Dehdashtian et al. |
| 6,383,213 B2 | 5/2002 | Wilson et al. |
| 6,387,120 B2 | 5/2002 | Wilson et al. |
| 6,391,050 B1 | 5/2002 | Broome |
| 6,391,051 B2 | 5/2002 | Sullivan, III et al. |
| 6,406,487 B2 | 6/2002 | Brenneman |
| 6,406,489 B1 | 6/2002 | Richter et al. |
| 6,409,741 B1 | 6/2002 | Crocker et al. |
| 6,416,529 B1 | 7/2002 | Holman et al. |
| 6,432,064 B1 | 8/2002 | Hibner et al. |
| 6,436,104 B2 | 8/2002 | Hojeibane |
| 6,443,980 B1 | 9/2002 | Wang et al. |
| 6,468,203 B2 | 10/2002 | Belson |
| 6,471,672 B1 | 10/2002 | Brown et al. |
| 6,475,166 B1 | 11/2002 | Escano |
| 6,475,639 B2 | 11/2002 | Shahinpoor et al. |
| 6,482,211 B1 | 11/2002 | Choi |
| 6,488,694 B1 | 12/2002 | Lau et al. |
| 6,508,835 B1 | 1/2003 | Shaolian et al. |
| 6,514,217 B1 | 2/2003 | Selmon et al. |
| 6,514,237 B1 | 2/2003 | Maseda |
| 6,514,281 B1 | 2/2003 | Blaeser et al. |
| 6,520,983 B1 | 2/2003 | Colgan et al. |
| 6,520,988 B1 | 2/2003 | Colombo et al. |
| 6,530,947 B1 | 3/2003 | Euteneuer et al. |
| 6,533,805 B1 | 3/2003 | Jervis |
| 6,540,719 B2 | 4/2003 | Bigus et al. |
| 6,540,779 B2 | 4/2003 | Richter et al. |
| 6,544,218 B1 | 4/2003 | Choi |
| 6,545,097 B2 | 4/2003 | Pinchuk et al. |
| 6,554,841 B1 | 4/2003 | Yang |
| 6,569,180 B1 | 5/2003 | Sirhan et al. |
| 6,582,459 B1 | 6/2003 | Lau et al. |
| 6,583,533 B2 | 6/2003 | Kornbluh et al. |
| 6,586,859 B2 | 7/2003 | Kornbluh et al. |
| 6,589,251 B2 | 7/2003 | Yee et al. |
| 6,589,262 B1 | 7/2003 | Honebrink et al. |
| 6,592,616 B1 | 7/2003 | Stack et al. |
| 6,596,020 B2 | 7/2003 | Vardi et al. |
| 6,599,315 B2 | 7/2003 | Wilson |
| 6,602,226 B1 | 8/2003 | Smith et al. |
| 6,602,247 B2 | 8/2003 | Lalonde |
| 6,607,506 B2 | 8/2003 | Kletschka |
| 6,613,067 B1 | 9/2003 | Johnson |
| 6,629,972 B2 | 10/2003 | Lehmann et al. |
| 6,629,981 B2 | 10/2003 | Bui et al. |
| 6,629,992 B2 | 10/2003 | Bigus et al. |
| 6,660,030 B2 | 12/2003 | Shaolian et al. |
| 6,664,718 B2 | 12/2003 | Pelrine et al. |
| 6,669,718 B2 | 12/2003 | Besselink |
| 6,679,836 B2 | 1/2004 | Couvillon, Jr. |
| 6,692,483 B2 | 2/2004 | Vardi et al. |
| 6,706,062 B2 | 3/2004 | Vardi et al. |
| 6,733,520 B2 | 5/2004 | Yang et al. |
| 6,749,628 B1 | 6/2004 | Cho et al. |
| 6,752,433 B2 | 6/2004 | Frost |
| 6,764,504 B2 | 7/2004 | Wang et al. |
| 6,770,027 B2 | 8/2004 | Banik et al. |
| 6,780,174 B2 | 8/2004 | Mauch |
| 6,783,542 B2 | 8/2004 | Eidenschink |
| 6,802,856 B2 | 10/2004 | Wilson |
| 6,835,173 B2 | 12/2004 | Couvillon, Jr. |
| 6,835,203 B1 | 12/2004 | Vardi et al. |
| 6,849,085 B2 | 2/2005 | Marton |
| 6,872,215 B2 | 3/2005 | Crocker et al. |
| 6,884,258 B2 | 4/2005 | Vardi et al. |
| 6,896,699 B2 | 5/2005 | Wilson et al. |
| 6,908,477 B2 | 6/2005 | McGuckin, Jr. et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,969,395 B2 | 11/2005 | Eskuri |
| 7,018,400 B2 | 3/2006 | Lashinski et al. |
| 7,018,402 B2 | 3/2006 | Vito et al. |
| 7,063,671 B2 | 6/2006 | Couvillon, Jr. |
| 7,070,613 B2 | 7/2006 | Weber et al. |
| 7,171,275 B2 | 1/2007 | Hata et al. |
| 7,225,518 B2 | 6/2007 | Eidenschink et al. |
| 7,238,197 B2 | 7/2007 | Sequin et al. |
| 7,314,480 B2 | 1/2008 | Eidenschink et al. |
| 7,326,242 B2 | 2/2008 | Eidenschink |
| 7,331,969 B1 | 2/2008 | Inganas et al. |
| 7,338,509 B2 | 3/2008 | Mattison |
| 7,344,557 B2 | 3/2008 | Yadin |
| 7,363,072 B2 * | 4/2008 | Movahed ................ 600/431 |
| 7,367,989 B2 | 5/2008 | Eidenschink |
| 7,379,852 B2 | 5/2008 | Freitas et al. |
| 7,396,362 B2 | 7/2008 | Jervis |
| 7,399,311 B2 | 7/2008 | Bertolino et al. |
| 7,422,579 B2 | 9/2008 | Wahr et al. |
| 2002/0019664 A1 | 2/2002 | Douglas |
| 2002/0038140 A1 | 3/2002 | Yang et al. |
| 2003/0033001 A1 | 2/2003 | Igaki |
| 2003/0055483 A1 | 3/2003 | Gumm |
| 2003/0055484 A1 | 3/2003 | Lau et al. |
| 2003/0125790 A1 * | 7/2003 | Fastovsky et al. ........... 623/1.11 |
| 2003/0181923 A1 | 9/2003 | Vardi |
| 2003/0195546 A1 | 10/2003 | Solar et al. |
| 2003/0236531 A1 | 12/2003 | Couvillon, Jr. |
| 2004/0068161 A1 | 4/2004 | Couvillon, Jr. |
| 2004/0220606 A1 | 11/2004 | Goshgarian |
| 2005/0015108 A1 | 1/2005 | Williams et al. |
| 2005/0038494 A1 | 2/2005 | Eidenschink |
| 2005/0060027 A1 | 3/2005 | Khenansho et al. |
| 2005/0096726 A1 | 5/2005 | Sequin et al. |
| 2005/0149161 A1 | 7/2005 | Eidenschink et al. |
| 2005/0149176 A1 | 7/2005 | Heggestuen et al. |
| 2005/0154442 A1 | 7/2005 | Eidenschink et al. |
| 2005/0157643 A1 | 7/2005 | Shah |
| 2005/0165439 A1 | 7/2005 | Weber et al. |
| 2005/0182473 A1 | 8/2005 | Eidenschink et al. |
| 2005/0187602 A1 * | 8/2005 | Eidenschink ............... 623/1.11 |
| 2005/0187603 A1 | 8/2005 | Eidenschink et al. |
| 2005/0273149 A1 | 12/2005 | Tran et al. |
| 2006/0064159 A1 | 3/2006 | Porter et al. |
| 2006/0074442 A1 | 4/2006 | Noriega et al. |
| 2006/0074475 A1 | 4/2006 | Gumm |
| 2006/0074476 A1 | 4/2006 | Holman et al. |
| 2006/0079836 A1 * | 4/2006 | Holman et al. ........... 604/96.01 |
| 2006/0100694 A1 | 5/2006 | Globerman |
| 2006/0173421 A1 | 8/2006 | Weber et al. |
| 2006/0206188 A1 | 9/2006 | Weber et al. |
| 2006/0271088 A1 | 11/2006 | Alfrhan |
| 2006/0271152 A1 | 11/2006 | Hilaire et al. |
| 2007/0088256 A1 | 4/2007 | Intoccia |
| 2007/0088423 A1 | 4/2007 | Levine et al. |
| 2007/0100301 A1 | 5/2007 | Gumm |
| 2007/0112418 A1 | 5/2007 | Eidenschink et al. |
| 2007/0118200 A1 | 5/2007 | Weber et al. |
| 2007/0208406 A1 | 9/2007 | Alkhatib et al. |
| 2007/0213811 A1 | 9/2007 | Gregorich et al. |
| 2007/0265637 A1 * | 11/2007 | Andreas et al. ............ 606/108 |

| | | |
|---|---|---|
| 2008/0086081 A1* | 4/2008 | Eidenschink et al. ..... 604/96.01 |
| 2008/0109060 A1 | 5/2008 | Yadin |
| 2008/0119923 A1 | 5/2008 | Tran et al. |

FOREIGN PATENT DOCUMENTS

| | | |
|---|---|---|
| CA | 2533306 | 3/2005 |
| CA | 2556693 | 9/2005 |
| CA | 2569567 | 12/2005 |
| DE | 29701758 | 3/1997 |
| EP | 0161863 | 7/1990 |
| EP | 0965311 | 12/1999 |
| EP | 1601312 | 9/2007 |
| ES | 2048086 | 3/1994 |
| ES | 2062930 | 12/1994 |
| FR | 2678508 | 1/1993 |
| GB | 2227020 | 7/1990 |
| JP | 8066351 | 3/1996 |
| JP | 8322783 | 12/1996 |
| JP | 10014863 | 1/1998 |
| WO | WO 97/45073 | 4/1997 |
| WO | WO 00/44307 | 8/2000 |
| WO | WO 01/58973 | 8/2001 |
| WO | WO 03/017872 | 3/2003 |
| WO | WO 03/055414 | 7/2003 |
| WO | WO 03/061529 | 7/2003 |
| WO | WO 03/094800 | 11/2003 |
| WO | WO 03/105922 | 12/2003 |
| WO | WO 03/105925 | 12/2003 |
| WO | WO 04/000141 | 12/2003 |
| WO | WO 2004/075792 | 9/2004 |
| WO | WO 2004/093968 | 11/2004 |
| WO | WO 2005/025458 | 3/2005 |
| WO | WO 2005/067818 | 7/2005 |
| WO | WO 2005/070334 | 8/2005 |
| WO | WO 2005/079902 | 9/2005 |
| WO | WO 2005/084130 | 9/2005 |
| WO | WO 2005/122958 | 12/2005 |
| WO | 2006020457 | 2/2006 |
| WO | WO 2006/020457 * | 2/2006 |
| WO | 2008113372 | 9/2008 |

OTHER PUBLICATIONS

Bar-Cohen et al., "Electro-Active Polymer (EAP) Actuators for Planetary Applications," SPIE, vol. 3669, pp. 57-63 Mar. 1999.
U.S. Appl. No. 12/199,563, filed Aug. 27, 2008, to Harrison.
Foley et al., "Bifurcation Lesion Stenting," The Thoraxcentre Journal, vol. 8/4, 5 pages, 1998.
Nakamura et al., "Techniques for Palmaz-Schatz Stent Deployment in Lesions with a Large Side Branch," Catheterization and Cardiovascular Diagnosis, vol. 34, pp. 353-361, 1995.
Oda et al., "Fork Stenting for Bifurcation Lesion," Journal of Interventional Cardiology, vol. 9, No. 6, pp. 445-454, Dec. 1996.
Palmaz et al., "Aortic Bifurcation Stenosis: Treatment with Intravascular Stents," Journal of Vascular and Interventional Radiology, vol. 2, No. 3, pp. 319-323, Aug. 1991.
Pomerantz et al., "Distortion of Palmaz-Schatz Stent Geometry Following Side-Branch Balloon Dilation Through the Stent in a Rabbit Model," Catheterization and Cardiovascular Diagnosis, vol. 40, pp. 422-426, Oct. 30, 1997.
Schampaert et al., "The V-Stent: A Novel Technique for Coronary Bifurcation Stenting," Catheterization and Cardiovascular Diagnosis, vol. 39, No. 3, pp. 320-326, Nov. 1996.
Bar-Cohen, "Application of Dielectric Elastomer EAP Actuators," Electroactive Polymer (EAP) Actuators as Artificial Muscles, Chapter 16, pp. 457-495, 2001.
Bar-Cohen, "EAP Applications, Potential, and Challenges," Electroactive Polymer (EAP) Actuators as Artificial Muscles, Chapter 21, pp. 615-659, 2001.
Bar-Cohen, "EAP History, Current Status, and Infrastructure," Electroactive Polymer Actuators (EAP) as Artificial Muscles, Chapter 1, pp. 3-43, 2001.
Bar-Cohen, "Electroactive Polymers as Artificial Muscles-Capabilities, Potentials and Challenges," Handbook on Biommetics, Section 11, Chapter 8, Aug. 2000.
Bar-Cohen, "Transition of EAP Material from Novelty to Practical Applications—Are we there Yet?," Proceedings of SPIE vol. 4329, pp. 1-6, Mar. 5-8, 2001.
Bar-Cohen, "WorldWide ElectroActive Polymers WW EAP (Artificial Muscles) Newsletter," vol. 3, No. 1, pp. 1-14, Jun. 2001.
Brock, "Review of Artificial Muscle Based on Contractile Polymers," 12 pages, May 9, 2002.
Buckley, "EAP DARPA," Defense Sciences Office, 8 pages, Jan. 2002.
Cho et al., "Development of Micro Inchworm Robot Actuated by Electrostrictive Polymer Actuator," Proceedings of SPIE , vol. 4329, pp. 466-474, Mar. 5-8, 2001.
Goodell, "Laser Thromolysis (LT) for Stroke," http://www.providence.org/Oregon/Programs_and_Services/Research/Laser_Center/Lt_Stroke..., 3 pages, Updated Mar. 26, 2001, printed Oct. 2, 2002.
Gulch et al., "Characterization of Electroactive Behavior and of Progress in Developments and Applications of Ionic Polymer Gels," Proceedings of SPIE vol. 4695, pp. 367-377, 2002.
http://ais.gmd.de/BAR/snake.html, "GMD-SNAKE, Robot-Snake with Flexible Real-Time Control," 3 pages, last updated Jan. 10, 2001, printed Dec. 27, 2001.
http://nanobio.snu.ac.kr/eng/research_5.html, "Electroactive Polymer," Nano Bioelectronics & Systems Research Center, 1 page, printed Feb. 5, 2004.
http://omlc.ogi.edu/projects/lt/, "Laser Thrombolysis," 9 pages, Dec. 12, 1996.
http://piaggio.ccii.unipi.it/cathe.htm, "Smart Catheters," 1 page, printed Aug. 27, 2001.
http://polysep.ucla.edu/Research20%Advances, "Polymers and Separations Research Lab (PolySep)," 12 pages, printed Feb. 5, 2004.
http://robby.caltech.edu/~chen/res-medical.html, "Snake-Like Robot Endoscopes," 2 pages, updated Aug. 14, 1996, printed Dec. 27, 2001.
http://virtualskies.arc.nasa.gov/reasearch/youDecide, "Electroactive Polymers 2: Ionic and Conductive Polymers," 2 pages, printed Feb. 5, 2004.
http://www.agip.sicences.univ-metz.fr/mihalach/Coperinicus_projet_engl.html, "Snake-Like Flexible Micro-Robot,".
http://www.azom.com/detailsasp?ArticleID=885, Electroactive Polymers—EAPs, 7 pages, Feb. 5, 2004.
http://www.designinsite.dk/htmsider/m1328.htminsider, 3 pages, printed Mar. 11, 2004.
http://www.erg.sri.com/automation/actuators.html, "Artificial Muscle Transducers," 3 pages, printed Feb. 5, 2004.
http://www.nasatech.com/Briefs/Oct01/NPO20613.html, "Miniature Electroactive-Polymer Rakes," 2 pages, Feb. 5, 2004.
Ikuta et al., "Shape Memory Alloy Servo Actuator System with Electric Resistance Feedback and Application for Active Endoscope," IEEE Internation Conference on Robotics and Automation, pp. 427-430, Apr. 24-29, 1988.
Immerstrand et al., "Conjugated-Polymer Micro- and Milliactuators for Biological Applications," MRS Bulletin, pp. 461-464, Jun. 2002.
Jager et al., "Applications of Polypyrrole Microactuators," SPIE, vol. 3669, pp. 377-384, Mar. 1999.
Jager et al., "Microfabricating Conjugated Polymer Actuators," Science, vol. 290, pp. 1540-1545, Nov. 24, 2000.
Kubler et al., "An Endoscopic Navigation System," Medicine Meets Virtual Reality, pp. 253, 255, 2001.
Kubler et al., "Endoscopic Robots," Proceedings of the 3$^{rd}$ International Conference on Medical Image Computing and Computer-Assisted Intervention—MICCAI, pp. 949-955, 2000.
Madden et al., "Conducting Polymer Actuators as Engineering Materials," Proceedings of SPIE vol. 4695, 2002.
Madden et al., "Polypyrrole Actuators: Modeling and Performance," Proceedings of SPIE vol. 4329, pp. 72-83, Mar. 5-8, 2001.
Madden, "Conducting Polymer Actuators," Abstract, 2 pages, Sep. 2000.
Mazzoldi et al., "Conductive Polymer Based Structures for a Steerable Catheter," Proceedings of SPIE vol. 3987, pp. 273-280, 2000.
Nam, "Electroactive Polymer (EAP) Actuators and Devices for Micro-Robot Systems," 1 page, Nov. 28, 2000.

Otero et al., "EAP as Multifunctional and Biommetic Materials," SPIE, vol. 3669, pp. 26-34, Mar. 1999.

Peirs et al., "Miniature Parallel Manipulators for Integration in a Self-Propelling Endoscope," 1 page, IMechs Workshop, Oct. 27, 1999.

Pelrine et al., "Applications of Dielectric Elastomer Actuators," Proceedings of SPIE vol. 4329, pp. 335-349, Mar. 5-8, 2001.

Rocchia et al., "Exploiting Conducting Polymer Fiber Radial Expansion for Bioinspired Actuation," Proceedings of SPIE vol. 5051, pp. 453-457, 2003.

Sahoo et al., "Actuators Based on Electroactive Polymers," Current Science, vol. 81, No. 7, pp. 743-746, Oct. 10, 2001.

Sansinena et al., "Chapter 7, Conductive Polymers," Electroactive Polymer Actuators (EAP) as Artificial Muscles, Edited by Bar-Cohen, pp. 193-221, 2001.

Santa et al., "Intravascular Microcatheters Steered by Conducting Polymer Actuators," 18th International Conference of the IEEE Engineering in Medicine and Biology Society, pp. 2203-2204, 1996.

Smela et al., "Electrochemically Driven Polypyrrole Bilayers for Moving and Positioning Bulk Micromachined Silicon Plates," Journal of Microelectromechanical Systems, vol. 8, No. 4, pp. 373-383, Dec. 1999.

Smela et al., "Thiol-Modified Pyrrole Monomers: 1. Synthesis, Characterization, and Polymerization of 1-(2-Thioethyl) Pyrrole and 3-(2-Thioethyl) Pyrrole," Langmuir, vol. 14, 2970-2975, May 26, 1998.

Smela, "Conjugated Polymer Actuators for Biomedical Applications," Advanced Materials, vol. 15, No. 6, pp. 481-494, Mar. 17, 2003.

Smela, "Microfabrication of PPy Microactuators and Other Conjugated Polymer Devices," Journal of Micromechanics and Microengineering, vol. 9, pp. 1-18, 1999.

Wax et al., "Compliant Actuators Based on Electroactive Polymers," Materials Research Society Proceedings, vol. 600, pp. 3-11, 2000.

Zhou et al., "Actuators for the Cochlear Implant," Synthetic Metals, vol. 135-136, pp. 39-40, 2003.

* cited by examiner

ELECTROACTIVE POLYMER ACTIVATION SYSTEM FOR A MEDICAL DEVICE

FIELD OF THE INVENTION

The present invention relates generally to medical devices and, more particularly, to intracorporal medical device, such as a guidewire, catheter, or the like having electroactive polymers.

BACKGROUND

The use of intravascular medical devices has become an effective method for treating many types of vascular disease. In general, one or more suitable intravascular devices are inserted into the vascular system of the patient and navigated through the vasculature to a desired target site. Using this method, virtually any target site in the patient's vascular system may be accessed, including the coronary, cerebral, and peripheral vasculature. Examples of therapeutic purposes for intravascular devices include percutaneous transluminal angioplasty (PTA) and percutaneous transluminal coronary angioplasty (PTCA).

When in use, intravascular devices, such as a catheter, may enter the patient's vasculature at a convenient location and then can be advanced over a guidewire to a target region in the anatomy. The path taken within the anatomy of a patient may be very tortuous, and as such, it may be desirable to combine a number of performance features in the intravascular device to aid in advancing the catheter over the guidewire. For example, it is sometimes desirable that the catheter has a relatively high level of pushability and torqueability. It is also sometimes desirable that a catheter is relatively flexible, for example, to aid in advancing the catheter over the guidewire to access a treatment site. For some applications, catheters may also be expected to exhibit tensile and/or compressive strength in certain regions.

A number of different elongated medical device structures, assemblies, and methods are known, each having certain advantages and disadvantages. However, there is an ongoing need to provide alternative elongated medical device structures, assemblies, and methods. In particular, there is an ongoing need to provide alternative medical devices including structure or assemblies configured to aid in advancing a catheter over a guidewire in a vessel of a patient and to aid in treating a treatment site of a patient, and methods of making and using such structures and/or assemblies.

BRIEF SUMMARY

The invention provides design, material, manufacturing method, and use alternatives for medical devices. An activation circuit for selectively providing an electrical current to one or more electroactive polymers (EAPs) in a medical device is disclosed. The activation circuit may include a sensor for sensing a measure related to a parameter of an elongated member and/or a balloon of the medical device. The electrical current may be provided to the one or more EAPs according to the sensed parameter of the elongated member and/or the balloon of the medical device. In some cases, the activation circuit may include a comparator for comparing the sensed measure to a threshold to determine when the electrical current is applied to the EAPs.

In some cases, the parameter may be a pressure, a fluid flow, and/or a temperature. In one embodiment, the medical device may include a rotatable balloon including EAP collars including EAP layers. In another embodiment, the medical device may include a drug delivery balloon including an EAP layer disposed about at least a portion of the balloon to selectively release one or more drugs into a vessel.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
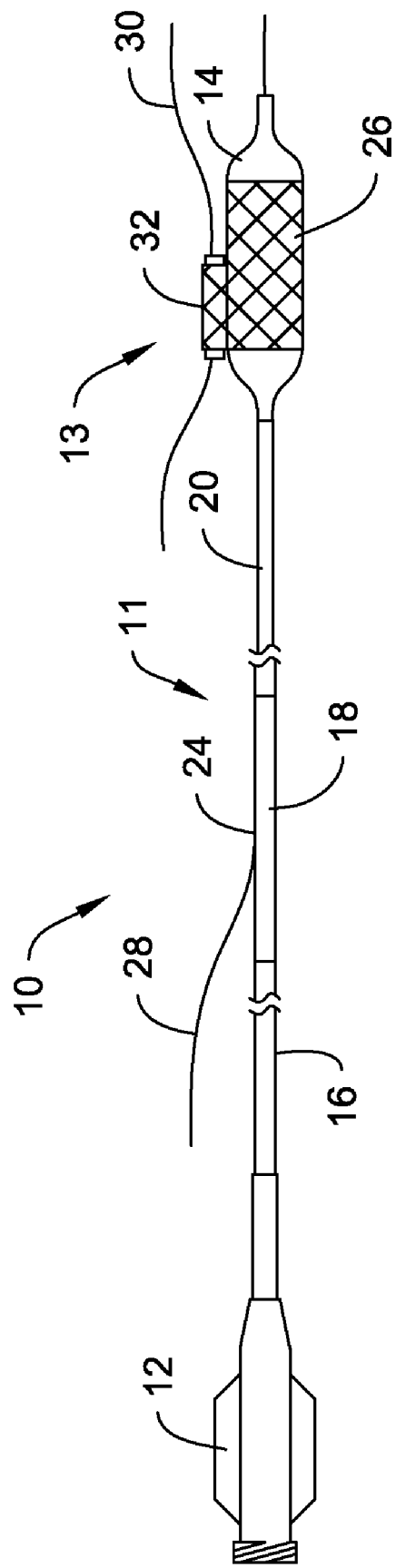
FIG. 1 is a schematic diagram of an illustrative balloon catheter including a stent.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIG. 1 is a perspective view of an illustrative embodiment of a balloon catheter 10 including a stent 26. In the illustrative embodiment, the balloon catheter 10 may include an elongated shaft 11 having a proximal end, a distal end, and one or more lumens extending therebetween. In the illustrative example, the one or more lumens may include an inflation lumen, a guidewire lumen, or any other lumen, as desired. An inflatable balloon 14 may be disposed adjacent to the distal end of the elongated shaft 11. As illustrated, the balloon 14 may be a stent delivery balloon. However, it is contemplated that the balloon 14 may be a typical angioplasty or other inflatable member, as desired.

A hub assembly 12 may be connected to the proximal end of the elongated shaft 11 to facilitate connection to an inflation device for inflating/deflating the balloon 14, and/or to facilitate insertion of a guidewire or other medical device therein. In some cases the inflatable balloon 14 may be fluidly connected to the hub assembly 12 via an inflation lumen of the elongated shaft 11.

In some embodiments, the elongate shaft 11 may include one or more sections to help achieve desired pushability, torqueability, and/or flexibility in the elongated shaft 11. As illustrated, the elongated shaft 11 may include a proximal section 16, a midshaft section 18, and a distal section 20. However, it is contemplated that the elongate shaft 11 may include a single section or any number of sections, as desired.

In the illustrative example, the proximal section 16 of the elongated shaft 11 may include an elongated tubular member having a lumen extending therethrough. In one example, the proximal section 16 of the elongated shaft 11 may include a hypotube, but this is not required. In some cases, the proximal section 16 may include one or more openings, slits, or other features to achieve a desired stiffness and flexibility, as desired. In some embodiments, the proximal section 16 may include a material to impart flexibility and stiffness characteristics according to the desired application. In the illustrative embodiment, the proximal section 16 may include a material to impart stiffness and pushability in the catheter 10. For example, the proximal section 16 may include a rigid and resilient material. In such an embodiment, the proximal section 16 may be made from a metal, a metal alloy, a polymer, a metal-polymer composite, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®, and the like), other nickel-chromium alloys, other nickel-molybdenum alloys, other nickel-cobalt alloys, other nickel-iron alloys, other nickel-copper alloys, other nickel-tungsten or tungsten alloys, and the like; cobalt alloys, such as cobalt-chromium alloys; cobalt-chromium-molybdenum alloys (e.g., UNS: R30003 such as ELGILOY®, PHYNOX®, and the like); platinum enriched stainless steel; combinations thereof, and the like; or any other suitable material. However, this is not meant to be limiting and it is to be understood that the proximal section 16 may include any suitable material described herein with reference to any other catheter component, such as, for example, a polymer or polymer blend discussed below, or any suitable material commonly used in medical devices, as desired.

In the illustrative embodiment, the midshaft section 18 of the elongate shaft 11 may be disposed distally of the proximal section 16. For example, the midshaft 18 may include a proximal end disposed adjacent to the distal end of the proximal section 16, a distal end, and one or more lumens extending therethrough. In some cases, the proximal end of the midshaft section 18 may be coupled to or otherwise connected to the distal end of the proximal section 16. There are numerous materials that can be used for the midshaft of catheter 10 to achieve the desired properties that are commonly associated with medical devices. Some example materials can include, but is not limited to, stainless steel, metal, nickel alloy, nickel-titanium alloy, hollow cylindrical stock, thermoplastics, high performance engineering resins, polymers, fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyoxymethylene (POM), polybutylene terephthalate (PBT), polyether block ester, or other polymer blends. For example, the polymer blend may include polyoxymethylene blended with a polyether polyester such as ARNITEL® available from DSM Engineering Plastics or HYTREL® available from DuPont. Other suitable polymers that may be blended with polyoxymethylene include polyether block ester, polyether block amide (PEBA, for example available under the trade name PEBAX®), polyetheretherketone (PEEK), polyetherimide (PEI), and the like. A suitable polyoxymethylene is commercially available under the trade name Delrin™ commercially available from DuPont Wilmington, Del. In some cases, the midshaft section 18 is manufactured so as to maintain the desired level of stiffness, flexibility, and torqueability according to multiple embodiments of the current invention and includes multiple layers over at least portions of its length which provide selected flexibility. However, it is to be understood that the above mentioned materials are not meant to be limiting and it is to be understood that the midshaft 18 may include any suitable material described herein with reference to any other catheter component or any suitable material commonly used in medical devices, as desired.

In the illustrative embodiment, the distal section 20 of the elongate shaft 11 may be disposed distally of the midshaft section 18. For example, the distal section 20 may include a proximal end disposed adjacent to the distal end of the midshaft section 18, a distal end, and one or more lumens extending therethrough. In some cases, the inflatable balloon 14 may be disposed about at least a portion of the distal section 20 adjacent to the distal end. The distal section 20 may include those materials that are commonly used in medical devices. Some example materials can include, but is not limited to, stainless steel, metal, nickel alloy, nickel-titanium alloy, hollow cylindrical stock, thermoplastics, high performance engineering resins, polymers, fluorinated ethylene propylene (FEP), polyethylene (PE), polypropylene (PP), polyvinylchloride (PVC), polyurethane, polytetrafluoroethylene (PTFE), polyether-ether ketone (PEEK), polyimide, polyamide, polyphenylene sulfide (PPS), polyphenylene oxide (PPO), polysufone, nylon, perfluoro(propyl vinyl ether) (PFA), polyoxymethylene (POM), polybutylene terephthalate (PBT), polyether block ester, or other polymer blends.

For example, the polymer blend may include polyoxymethylene blended with a polyether polyester such as ARNITEL® available from DSM Engineering Plastics or HYTREL® available from DuPont. Other suitable polymers that may be blended with polyoxymethylene include polyether block ester, polyether block amide (PEBA, for example available under the trade name PEBAX®), polyetheretherketone (PEEK), polyetherimide (PEI), and the like. A suitable polyoxymethylene is commercially available under the trade name Delrin™ commercially available from DuPont Wilmington, Del. In some cases, the distal section 20 is manufactured so as to maintain the desired level of stiffness, flexibility, and torqueability according to multiple embodiments of the current invention and includes multiple layers over at least portions of its length which provide selected flexibility. However, this is not meant to be limiting and it is to be understood that the distal section 20 may include any suitable material described herein with reference to any other catheter component or any suitable material commonly used in medical devices, as desired.

Furthermore, it should be understood that other suitable structures or components, may be incorporated into the elongate shaft 11 of the catheter 10. For example, a braided member, one or more coils, and/or marker members, or the like may be disposed along a portion of or the entire length of the elongated shaft 11. In example cases when a braided member is provided, the braided member may be provided in the proximal section 16, in the midshaft 18, in the distal section 20, or any combination thereof, as desired. The braided member may take on a number of forms. Typically the braided member will include a lubricious inner layer and a polymeric outer layer, with a braid composed of a number of filaments or strands braided between the inner and outer layers. A helical, double helical, coiled, or woven member may be used in place of the braid, if desired.

Additionally, the foregoing elongated member 11 is merely illustrative and is not meant to be limiting in any manner. It is to be understood that any suitable elongated member may be used in the catheter 10, as desired.

In the illustrative embodiment, a guidewire 28 may be slidably disposed through a lumen of the elongate member 11. As illustrated, the guidewire 28 may be disposed in a first port at the distal end of the catheter 10 and through a second port 24 shown in the elongate shaft 11. As illustrated, the guidewire port 24 is provided in the midshaft section 18, however, the guidewire port 24 may be provided in the proximal section 16, the distal section 20, as well as in any other suitable location of the elongated member 11, as desired.

Figure 2:
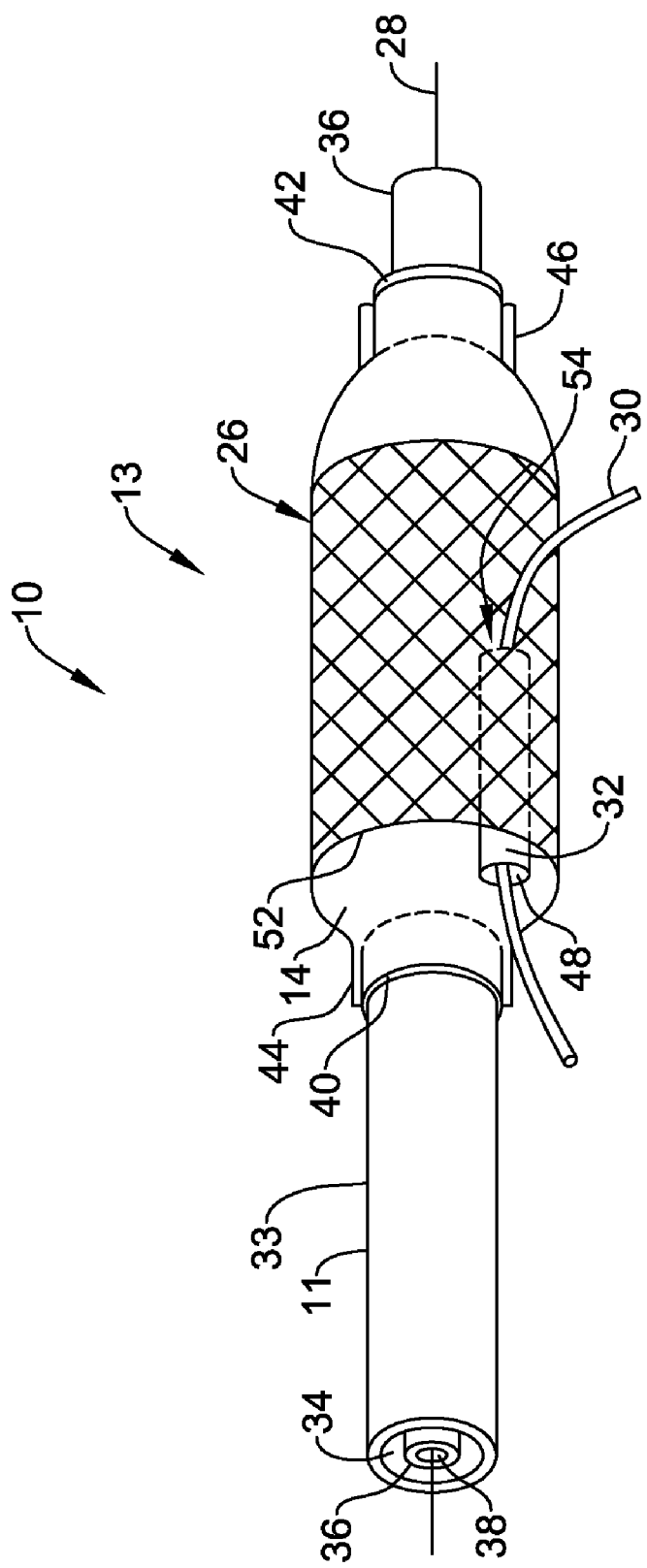
FIG. 2 is a perspective view of the distal end of the illustrative catheter of FIG. 1.

FIG. 2 is a perspective view of the distal end 13 of the illustrative catheter 10 shown in FIG. 1. In the illustrative embodiment, the elongated member 11 may include an inner shaft 36 and an outer shaft 33. The balloon 14 may be rotatably disposed about the elongated member 11 and configured to engage one or both of the inner shaft 36 and the outer shaft 33. As illustrated, the inner shaft 36 may include a lumen 38 defining a guidewire lumen of the elongate shaft 11 and the outer shaft 33 may include a lumen 34 defining an inflation lumen of the elongate shaft 11.

In the illustrative embodiment, the balloon 14 may include a proximal waist 44 and a distal waist 46 configured to engage a portion of the elongated shaft 11. As illustrated, the proximal waist 44 may be disposed about a collar 40 and the distal waist 46 may be disposed about a collar 42. In the illustrative embodiment, collar 40 and collar 42 may include an electro-active polymer (EAP) actuator that is actuatable between an expanded state and a contracted state. In some cases, the expanded state may be an activated state and the contracted state may be a non-activated state. In the contracted or non-activated state, the proximal waist 44 and the distal waist 46 of the balloon 14 may be rotatable about collar 40 and collar 42, respectively. In some cases, in the contracted or non-activated state, the balloon 14 may be fluidly unsealed. In the expanded or activated state, the proximal waist 44 and the distal waist 46 of the balloon 14 may be configured to be fluidly sealed to and/or non-rotatable about collars 40 and 42, respectively.

EAPs are polymers that are characterized by their ability to change shape in response to an electrical stimulus. For example, in some embodiments the EAP material may expand about 0.5% to about 20% when exposed to an electric current of 0.001 microAmps to 1 milliAmps (−2 to +2 V). Some examples of materials that may be used in EAPs may include, but is not limited to, polypyrroles, polyanilines, polythiophenes, polyethylenedioxythiophenes, poly(p-phenylene vinylene)s, polysulfones, polyacetylenes, Nafion, Bucky paper and any other ionic electro-active polymer that is considered to have low voltage, low speed, high stress (up to 500 MPa), characteristics. Furthermore, it is contemplated that any electroactive polymer that exhibits contractile or expansile properties may be used in connection with the various active regions of the invention, including those listed above.

These EAPs may have a number of properties that make them attractive for use in the medical devices such as, for example, they are lightweight, flexible, small and easily manufactured; energy sources are available which are easy to control, and energy can be easily delivered to the EAPS; small changes in potential (e.g., potential changes on the order of 1V) can be used to effect volume change in the EAPs; they are relatively fast in actuation (e.g., full expansion/contraction in a few seconds); EAP regions can be created using a variety of techniques, for example, electrodeposition; EAP regions can be patterned, for example, using photolithography; and many other properties. EAP materials and some of their notable characteristics are described in an article entitled Electro-Active Polymer Actuators for Planetary Applications by Y. Bar-Cohen et al. and published in Paper No. 3669-05 of the Proceedings of SPIE Annual International Symposium on Smart Structures and Materials, March 1999, Newport Beach, Calif. SPIE Copyright 1999, the entire contents of which being incorporated herein by reference.

In the illustrative embodiment, the catheter 10 may include a secondary tubular member 32 including a proximal end, a distal end, and a secondary guidewire lumen 48 configured to receive a second guidewire 30 therethrough. In some embodiments, the secondary tubular member 32 may be configured to engage a portion of the balloon 14. However, it is also contemplated that the secondary tubular member 32 may engage a portion of the elongated member 11, if desired. Although not illustrated, in some cases, it is contemplated that two or more secondary tubular members 32 may engage a portion of the balloon 14. In this case, the two or more secondary tubular members 32 may be disposed about one another to provide a variety of flexibility, hardness, and/or stiffness characteristics as desired. As such the secondary tubular member may be constructed of any of a wide variety of materials including, but not limited to, metal(s), polymer(s), natural rubber, silicone, multilayer materials, urethanes, PEBAX, HDPE, etc.

In the illustrative embodiment, stent 26 may be disposed about at least a portion of balloon 14 and/or secondary tubular member 32. As illustrated, a proximal portion 52 of stent 26 may be disposed about both the balloon 14 and the secondary tubular member 32 and a distal portion of the stent 26 may be disposed about only the balloon 14. In this configuration, a distal end 50 of the secondary tubular member 32 may extend through an intermediate opening 54 of the stent 26. In the illustrative example, the intermediate opening 54 of the stent 26 may be provided at any suitable location between a distal end and a proximal end of the stent 36, as desired.

In some cases, stent 26 may be at least partially constructed of a plurality of interconnected struts, connectors, or other members. The stent 26 defines a proximal opening, a distal opening, and a flow path therebetween. The intermediate opening 54 may also be in fluid communication with the flow path, if desired. In some embodiments, the stent 26 may be a standard "single vessel" stent that is provided with an intermediate opening in the manner described above, or the stent 26 may also be a bifurcated stent having a trunk and/or stem portion, with one or more leg portions and/or branch openings adjacent thereto, through which the secondary guidewire 30 may be passed. Such bifurcated stents and stent assemblies are well known in the art. Furthermore, it is contemplated that the stent 26 may be a standard single vessel stent with no intermediate opening 54 or any other suitable stent, as desired. In some situations, it is contemplated that the catheter may not include the secondary tubular member 32, if desired.

In the illustrative embodiment, guidewire 30 may be slidably disposed through the lumen 48 of the secondary tubular member 32. However, in some cases, the guidewire 30 may be merely slid between the balloon 14 and the stent 26 without the use of the secondary tubular member 32, if desired. In some embodiments, where the stent 26 is to be positioned substantially proximal to a side branch of the bifurcation, the guidewire 30 and/or secondary tubular member 32 may be configured to extend under the entire length of the stent 26.

In the illustrative dual guidewire embodiment, in operation, the guidewire 28 may be initially advanced through a vessel distal of a side branch of a bifurcation and the secondary guidewire 30 may be advanced through the vessel and into the side branch of the bifurcation. The catheter 10 may then be advanced along the guidewires 28 and 30 through the vessel until the balloon 14 and the stent 26 reach a desired position in the vessel, such as, for example, adjacent to the side branch of the bifurcation. While advancing the catheter 10 over the guidewires 28 and 30, the balloon 14 may be in a rotatable and/or non-fluidly sealed state allowing the balloon 14 to rotate relative to the elongated shaft 11 of the catheter 10. In particular, the catheter 10 may be advanced over crossed or otherwise twisted guidewires 28 and 30. In addition, the balloon 14 and stent 26 may be rotated to align the intermediate opening 54 of the stent 26 with the side branch vessel at the bifurcation while being advanced over the guidewires 28 and 30. Once properly positioned, the EAP of collars 40 and 42 may be actuated to a fluidly sealed and/or rotatably fixed state, as will be described in further detail. In some cases, inflating the balloon 14 may deploy the stent 26 and/or fluidly seal the balloon 14. However, any other suitable deployment may be used, as desired.

Figure 3:
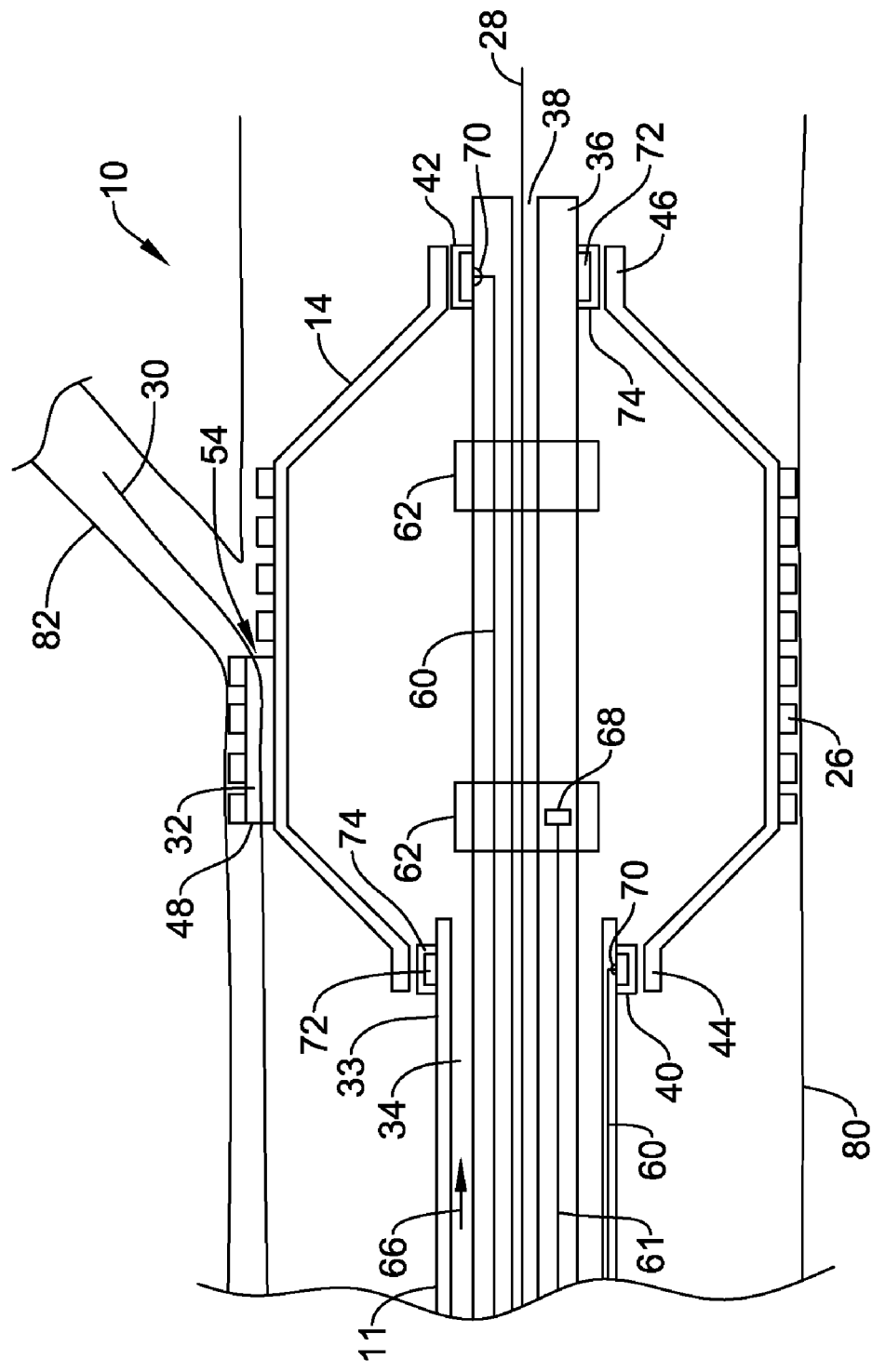
FIGS. 3 and 4 are a longitudinal cross-sectional views of the catheter of FIG. 2 disposed within a vessel adjacent to a bifurcation.

FIG. 3 is a longitudinal cross-sectional view of the catheter 10 of FIG. 2 disposed within a vessel 80 adjacent to a bifurcation. In the illustrative embodiments, collar 40 and collar 42 are shown in a contracted or a non-activated state. In this state, collar 40 and collar 42, including EAP material, are not exposed to an electrical current sufficient to activate the EAP material 74 of the collars 40 and 42. As illustrated, collars 40 and 42 include a work electrode 72 and an EAP coating or layer 74. A counter electrode 68 can be provided to a return path to complete the circuit.

In the illustrative embodiment, actuation of the EAP material of collars 40 and 42 may utilize the following elements: a source of electrical potential, an active region that includes the EAP 74, counter electrode 68, and an electrolyte in contact with the active region and/or the counter electrode 68. In the illustrative embodiment, the source of electrical potential may be a battery provided in the hub 12 (shown in FIG. 1). However, it is contemplated that any suitable source of electrical potential may be used, as desired. Additionally, the source of electrical potential may be provided in other location of the catheter 10, such as, for example, in or on the elongated shaft 11, or any suitable location remote of the catheter 10, as desired.

In the illustrative embodiment, the EAP layer 74 and/or work electrode 72 of collars 40 and 42 may be electrically connected to the electrical potential, such as, for example, the battery provided in the hub by an electrical conductor line 60. Example conductor lines are disclosed in application Ser. No. 12/199,563 entitled "Electrically Conductive Pathways in Medical Devices", filed on the even date herewith, which is hereby incorporated by reference.

The work electrode 72 may be disposed about at least a portion of the elongate shaft 11 and in contact with the EAP layer 74. For example, for collar 40, the work electrode 72 may be disposed about a portion of the outer shaft 33 and, for collar 42, the work electrode 72 may be disposed about a portion of the inner shaft 36. The work electrode 72 formed from any suitable electrical conductive material or materials and is preferably biocompatible. For example, a conducting polymer, a conducting gel, or a metal, such as stainless steel, gold, silver, platinum, nitinol, or any other conductive metal, as desired.

In some cases, EAP layer 74 may be disposed about at least a portion of work electrode 72. In one example, the EAP layer 74 may completely encapsulate the work electrode 72, if desired. The active region including the EAP layer 74 may be a polypyrrole-containing active region. Polypyrrole-containing active regions can be fabricated using a number of known techniques, for example, extrusion, casting, dip coating, spin coating, or electro-polymerization/deposition techniques. Polypyrrole-containing active regions can also be patterned, for example, using lithographic techniques, if desired.

The electrolyte, which may be in contact with at least a portion of the EAP layer 74 of the active region, allows for the flow of ions and thus acts as a source/sink for the ions. The electrolyte may be, for example, a liquid, a gel, or a solid, so long as ion movement is permitted. Where the electrolyte is a liquid, it may be, for example, an aqueous solution containing a salt, for example, an NaCl solution, a KCl solution, a sodium dodecylbenzene sulfonate solution, a phosphate buffered solution, physiological fluid, and so forth. Where the electrolyte is a gel, it may be, for example, a salt-containing agar gel or polymethylmethacrylate (PMMA) gel. Where the electrolyte is a solid, it may be, for example, a polymer electrolyte. In some embodiments, a saline or other fluid 66 of an electrically conductive nature used to expand the balloon 14 may electrically connect the work electrode 72 and/or EAP layer 74 to a counter electrode 68 positioned within the interior of balloon 14. In some embodiments, one or more marker bands 62 may be used as the counter electrode 68, if desired. A conductor wire 61 may be connected to counter electrode 68 to electrically complete the circuit. In some embodiments, the conductive nature of some bodily fluids may be utilized to complete the circuit.

In some examples, the EAP layer 74 may be configured to expand in at least one radial dimension (i.e., in at least one dimension that is orthogonal to the longitudinal axis of the device) upon activation of the active region. In other examples, the EAP layer 74 may be configured to expand in at least one axial dimension (i.e. in at least one dimension parallel to the longitudinal axis of the device) upon activation of the active region. Furthermore, it is contemplated that the EAP layer 74 may be configured to expand in at least one radial dimension and at least one axial dimension upon activation of the active region, as desired. Furthermore, upon the deactivation of the active region (i.e. removal of electrical potential), the EAP layer 74 may be configured to contract in the at least one radial dimension and/or at least one axial dimension. Some examples of suitable techniques, methods, and structures for EAPs are disclosed in application Ser. No. 10/763,825 titled "Electrically Actuated Medical Devices", which is hereby incorporated by reference.

In the illustrative embodiment, upon activation of the active region, or EAP layer 74, the collars 40 and 42 may be configured to expand in a radial and/or an axial direction. In this activated state, collars 40 and 42 may contact one or more of proximal waist 44 and/or distal waist 46. Upon contact, the collars 40 and 42 may fluidly seal the rotatable balloon 14. Additionally, in some cases, the contact may inhibit and/or prevent rotation of the balloon 14 relative to the elongate shaft 11, if desired. In some cases, the collars 40 and 42 may cause a friction fit with proximal waist 44 and/or distal waist 46.

When activated, battery may transmit an electric current through wires 60 to the collars 40 and 42. The current may cause the EAP layer 74 of the collars 40 and 42 to expand in an axial and/or radial dimension engaging the proximal waist 44 and/or the distal waist 46 of the balloon 14, respectively. The electric circuit may be completed as the result of a saline or other fluid 66 of an electrically conductive nature used to expand the balloon 14. The fluid 66 may electrically connect the collars 40 and 42 to a conductive member or conductor 68 positioned within the interior of balloon 14. In some embodiments, the conductor 68 may be in electric communication with one or more marker bands 62. The conductor wire 61 may be connected to counter electrode 68 to electrically complete the circuit.

Figure 4:
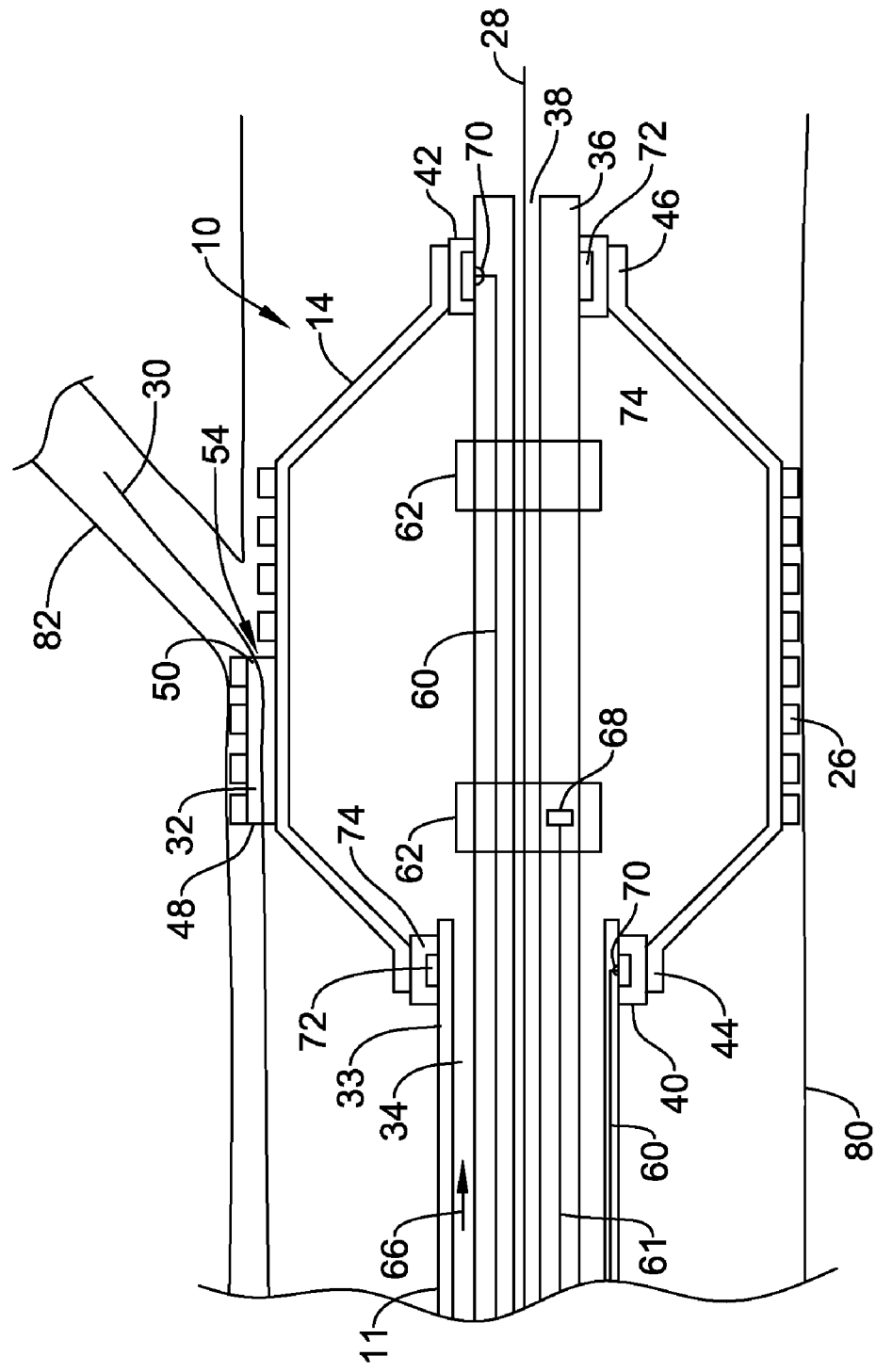

FIG. 4 is a longitudinal cross-sectional view of the catheter 10 of FIG. 3 in an activated state. As illustrated, the EAP layer 74 of collar 40 and collar 42 may be activated to be in an expanded state fluidly sealing and/or rotatably fixing the balloon 14 to the elongate shaft 11.

In some embodiments, the EAP layer 74 may be automatically activated and expanded when the balloon is inflated. For example, an activation circuit may be provided between the source of electrical potential, such as the battery, and the EAP layers 74 to selectively provide an electrical current to the EAP layer 74. In some embodiments, the activation circuit may be provided in or adjacent to the hub 12, in or adjacent to the elongated shaft 11, or in or adjacent to the balloon 14, as desired.

While the EAP layer 74 in FIGS. 3 and 4 is shown as being disposed on an outer surface, a proximal surface, and a distal surface of the work electrode 72, it is contemplated that any suitable shape and/or size EAP layer 74 may be used, as desired. Example medical devices including EAP layers are disclosed in application Ser. No. 10/915,209, titled "Rotatable Catheter Assembly" and application Ser. No. 10/785,449 titled "Rotatable Catheter Assembly", which are hereby incorporated by reference.

Figure 5:
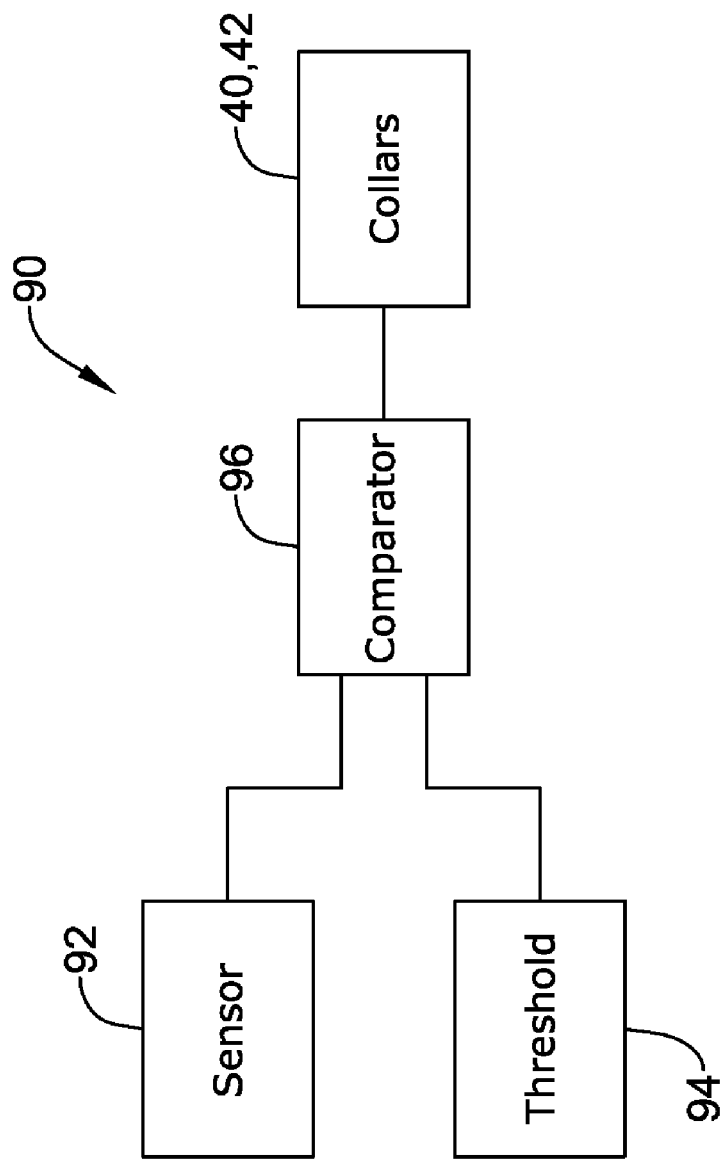
FIG. 5 is a block diagram of an illustrative embodiment of an activation circuit for activating the EAP layers of collars of the catheter of FIG. 1.

FIG. 5 is a block diagram of an illustrative embodiment of an activation circuit 90 for activating the EAP layers 74 of collars 40 and 42 of the catheter 10 of FIG. 1. In the illustrative embodiment, activation circuit 90 may include a sensor block 92 for sensing a measure related to a parameter of the inflation fluid 66 (shown in FIGS. 3 and 4) and/or catheter 10, a threshold block 94 for setting one or more parameter activation and/or deactivation thresholds, and a comparator block 96 for comparing the sensed measure relating to the parameter of the inflation fluid and/or catheter to the one or more parameter activation and/or deactivation thresholds. In some embodiments, the measure related to a parameter of the inflation fluid 66 and/or catheter may include a pressure, a rate of flow, a temperature, a change in concentration of a chemical substance, as well as any other suitable parameter, as desired.

In the illustrative embodiment, sensor block 92 may sense a measure related to a parameter of the inflation fluid and may provide an electrical output signal to the comparator block 96 corresponding to the sensed measure. In some embodiments, the sensor block 92 may include a microelectromechanical system (MEMS) sensor having a piezoelectric or other material with a resistivity sensitive to changes in the measure related to the parameter of the inflation fluid and/or catheter. For example, if the parameter to be sensed is the pressure of the inflation fluid and/or pressure of a portion of the catheter, such as, for example, the inflation lumen, and a MEMS pressure sensor is used, the resistance of the piezoelectric or other material may be a function of the pressure. When a current is passed through the pressure sensitive MEMS sensor, the output voltage may vary in response to a change in pressure.

Furthermore, it is contemplated that the sensor block 92 may include a pressure sensor, a flow sensor, a temperature sensor, and/or any other suitable sensor to measure any desired parameter of the inflation fluid, as desired. For example, the flow sensor may measure the flow rate of the inflation fluid in a portion of the catheter, such as in the hub, in the lumen of the elongated shaft, and/or in the balloon. In some cases, the temperature sensor may sense a temperature of a portion of the catheter. For example, the temperature sensor may sense a temperature of at least a portion of the inflation lumen of the catheter so that when the inflation fluid is provided to inflate the balloon, the temperature sensor may sense a temperature change in the inflation lumen. In some embodiments, the sensor block 92 may be provided in or adjacent to the hub 12, in or adjacent to the elongated shaft 11, and/or in or adjacent to the balloon 14 to sense the measure related to the inflation fluid and/or catheter.

In the illustrative embodiment, the threshold block 94 may include a predetermined or predefined threshold value. The threshold block 94 may provide an output signal having a voltage corresponding to the predetermined or predefined threshold value. Example threshold pressures may include, but are not limited to, 2 standard atmospheres (ATM), 3 ATM, 4 ATM, 5 ATM, 6 ATM, 7 ATM, 8 ATM, 9 ATM, 10 ATM, or any other suitable pressure, as desired. For example, if the balloon has a target inflation pressure of about 20 ATM, the threshold pressure may be set to any pressure lower than the target inflation pressure.

In the illustrative embodiment, the comparator block 96 may include a first input connected to the sensor block 92 and a second input connected to the threshold block 94. An output of the comparator may be electrically connected to the collars 40 and 42 via wires 60 (shown in FIGS. 3 and 4) to selectively activate the EAP layer 74 of the collars 40 and 42. In some cases, the comparator block 96 may include an operational amplifier to compare the sensor block 92 output voltage to the threshold block 94 output voltage. The operational amplifier may output a voltage level according to the compared voltages. For example, if the sensor block 92 output voltage is greater than the threshold block 94 output voltage, the operational amplifier may output a high voltage, or a voltage sufficient to activate the EAP layers 74 of the collars 40 and 42. In some cases, if the sensor block 92 output voltage is less than the threshold block 94 output voltage, the operational amplifier may output a low voltage, or a voltage about zero volts or other voltage that is insufficient to activate the EAP layers 74 of the collars 40 and 42.

In some embodiments, it is contemplated that the activation circuit 100 may include multiple thresholds, such as, for example, a turn on threshold and a turn off threshold. The turn on threshold may be a threshold used to switch the operational amplifier from the low to the high (i.e. turn on) and the turn off voltage may be a threshold to switch the operational amplifier from high to low (i.e. turn off). In some cases, the turn on threshold may be greater than the turn off threshold. In the illustrative embodiment, the multiple threshold voltages may provide an amount of hysteresis for the operational amplifier.

Additionally, it is contemplated that the comparator block 96 may include any suitable switch or switching mechanism to switch the output of the comparator block 96 from low to high and high to low according to a sensed measure related to a parameter of the inflation fluid and/or catheter, as desired.

Furthermore, while the activation circuit 90 has been described with reference to sensing a measure related to a parameter of the inflation fluid, it is contemplated that other parameters of the catheter 10 may be sensed to activate the EAP layers. For example, it is contemplated that a stress/strain of the elongated shaft and/or balloon may be sensed to activate the EAP layers, if desired.

Figure 6:
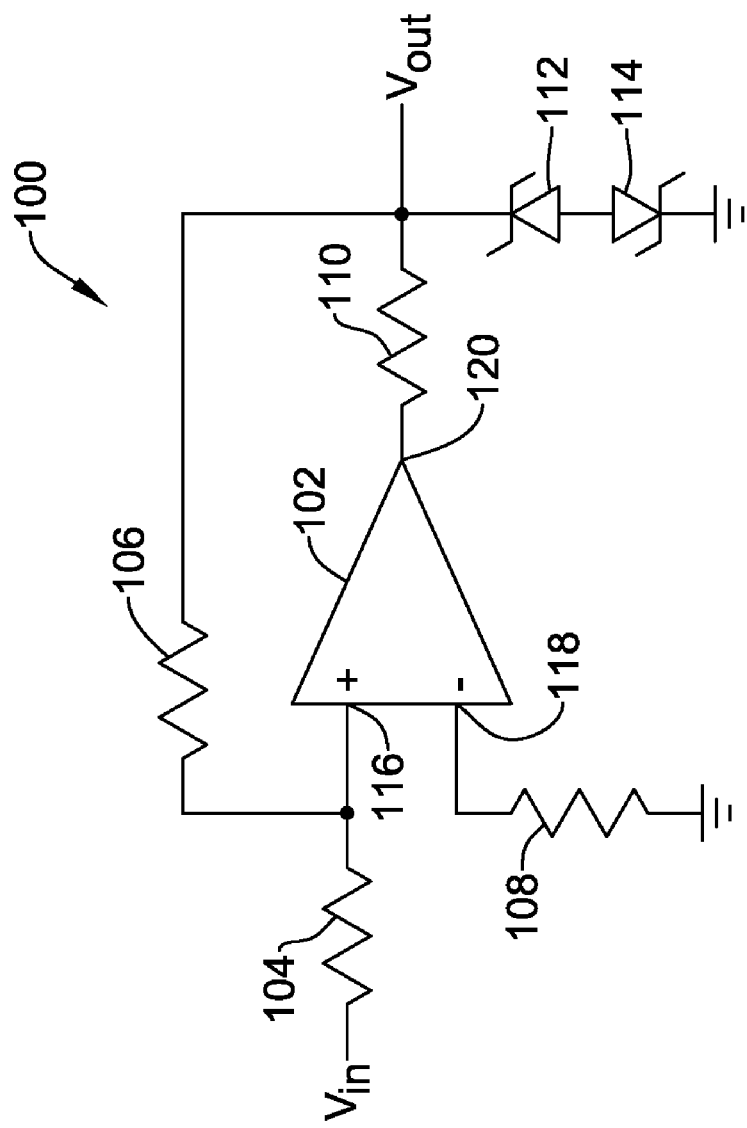
FIG. 6 is a schematic diagram of an illustrative circuit of a Schmitt trigger that may be included in the comparator of FIG. 5.

FIG. 6 is a schematic diagram of an illustrative circuit 100 of a Schmitt trigger that may be included in the comparator 96 of FIG. 5. As illustrated, the circuit may include a voltage input $V_{IN}$ connected to a first side of resistor 104. The second side of resistor may be connected to a positive input 116 of an operational amplifier 102. A negative input 118 of the operational amplifier 102 may be connected to ground via a resistor 108. An output 120 of the operational amplifier 102 may be connected to a first side of resistor 110. A second side of resistor 110 may be an output for the circuit 100 having an output voltage $V_{OUT}$. A resistor 106 may have a first side connected to the positive input 116 of the operational amplifier 102 and a second side connected to the output of the circuit 100. A pair of zener diodes 112 and 114 may be connected between the output of the circuit 100 and ground. Zener diode 112 may have a cathode connected to the output of the circuit and an anode connected to an anode of zener diode 114, which may have a cathode connected to ground.

In the illustrative embodiment, when the input voltage $V_{IN}$ is greater than a turn on threshold voltage (i.e. positive input 116 is greater than negative input 118), the output voltage $V_{OUT}$ may be high. When the input voltage is less than a turn off threshold voltage (i.e. positive input 116 is less than the negative input 118), the output voltage $V_{OUT}$ may be low. When the input voltage $V_{IN}$ is between the turn on threshold voltage and the turn off threshold voltage, the output voltage $V_{OUT}$ will retain the previous voltage level. In this example, the circuit 100 may have an amount of hysteresis, which may be controlled by resistances of resistors 104 and 106. In other words, the output voltage $V_{OUT}$ will switch from low to high when the input voltage $V_{IN}$ becomes greater than the turn on threshold voltage and will switch from high to low when the input voltage $V_{IN}$ drops below the turn off threshold voltage.

Figure 7:
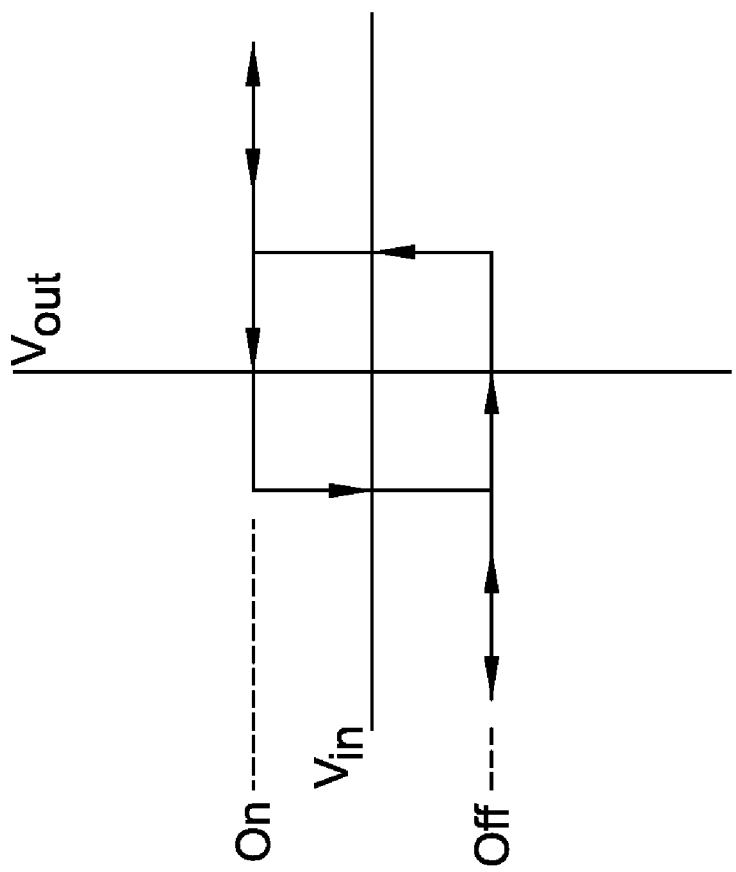
FIG. 7 is an illustrative graph showing the output voltage of the circuit of FIG. 6 as a function of the input voltage.

FIG. 7 is an illustrative graph showing the output voltage $V_{OUT}$ of the circuit 100 of FIG. 6 as a function of the input voltage $V_{IN}$. As illustrated, the circuit may include an amount of hysteresis. As illustrated, the circuit may turn on at a first input voltage and turn off at a second input voltage that is less than the first input voltage. The different between the turn on voltage and the turn off voltage may be adjusted according to resistors 104 and 106 of FIG. 6.

Figure 8:
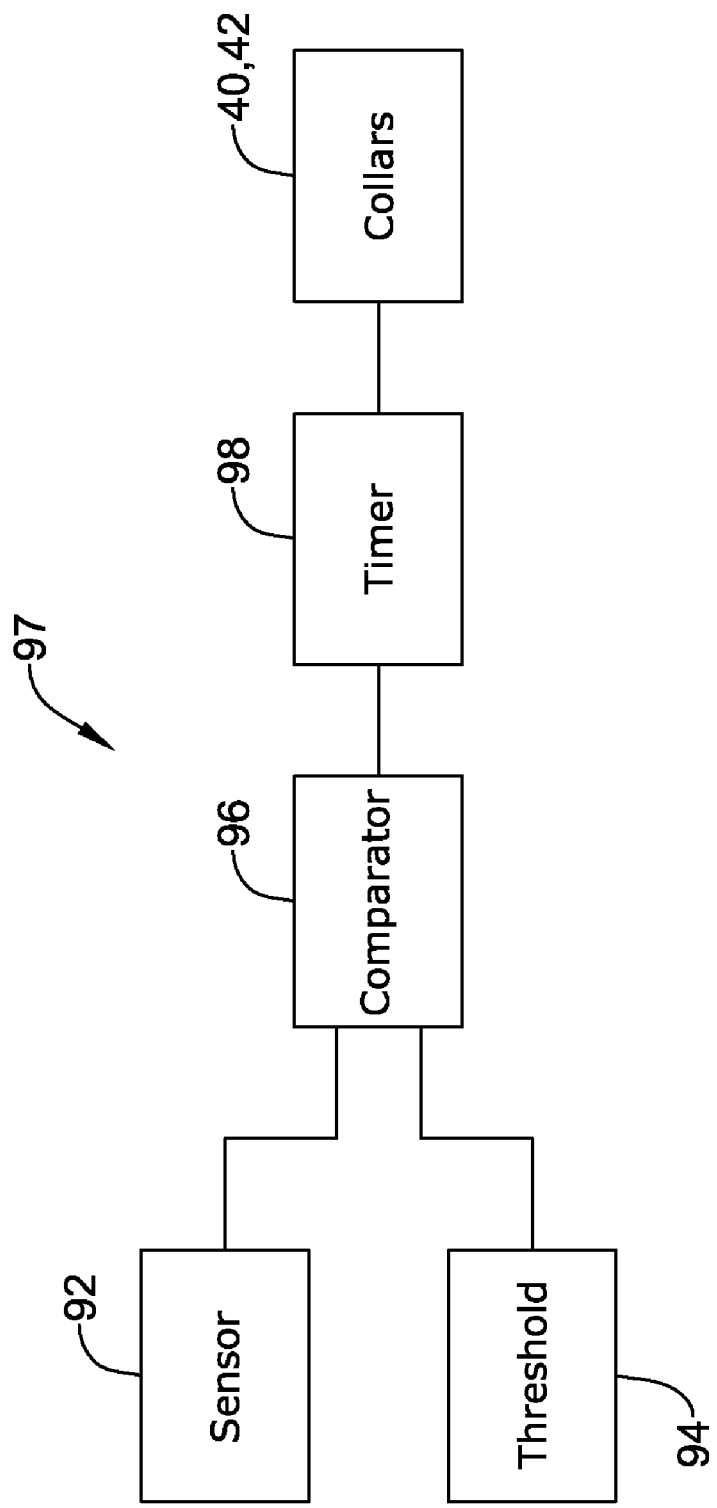
FIG. 8 is block diagram of another illustrative embodiment of an activation circuit.

FIG. 8 is block diagram of another illustrative embodiment of an activation circuit 97. The illustrative activation circuit 97 may be similar to the activation circuit 90 of FIG. 5 with the addition of a timer block 98. The timer block 98 may include an input coupled to the output of the comparator block 96 and an output coupled to the collars 40 and 42. In some embodiments, the timer may be programmed or otherwise configured to activate the one or more EAP layers 74 for a period of time when the sensed measure related to a parameter of the inflation fluid and/or catheter is greater than the threshold value. In some cases, the timer may be programmed or otherwise configured to activate the one or more EAP layers 74 at intervals of time when the sensed measure related to a parameter of the inflation fluid and/or catheter is greater than the threshold value. For example, when the output of the comparator block 96 switches to a high output, the timer block 98 may be reset to zero and may start counting. The timer block 98 may transmit the high output of the comparator block 96 to the collars 40 and 42 for a period of time until the timer block 98 reaches a time limit. In some cases, the time limit may be 5 seconds, 10 seconds, 20 seconds, 30 seconds, or any other amount of time, as desired. In some cases, once the time limit of the timer block 98 is reached, the timer block 98 may prevent a voltage from being applied to the collars 40 and 42 until the timer block 98 is reset when the comparator block 96 output switches from low to high. Alternatively, in some cases, the timer block 98 may apply the high output of the comparator block 96 to the collars 40 and 42 at intervals. For example, the timer block 98 may initially transmit the high output of the comparator block 96 for a first interval of time, then the timer block 98 may not transmit the high output for a second interval of time, then the timer block 98 may transmit the high output for a third interval of time, and so forth. The first interval of time, the second interval of time, and the third intervals of time may be the same or different intervals, as desired. In some cases, the first interval of time may be longer than the third interval of time. However, any suitable intervals of time may be used, as desire.

Figure 9:
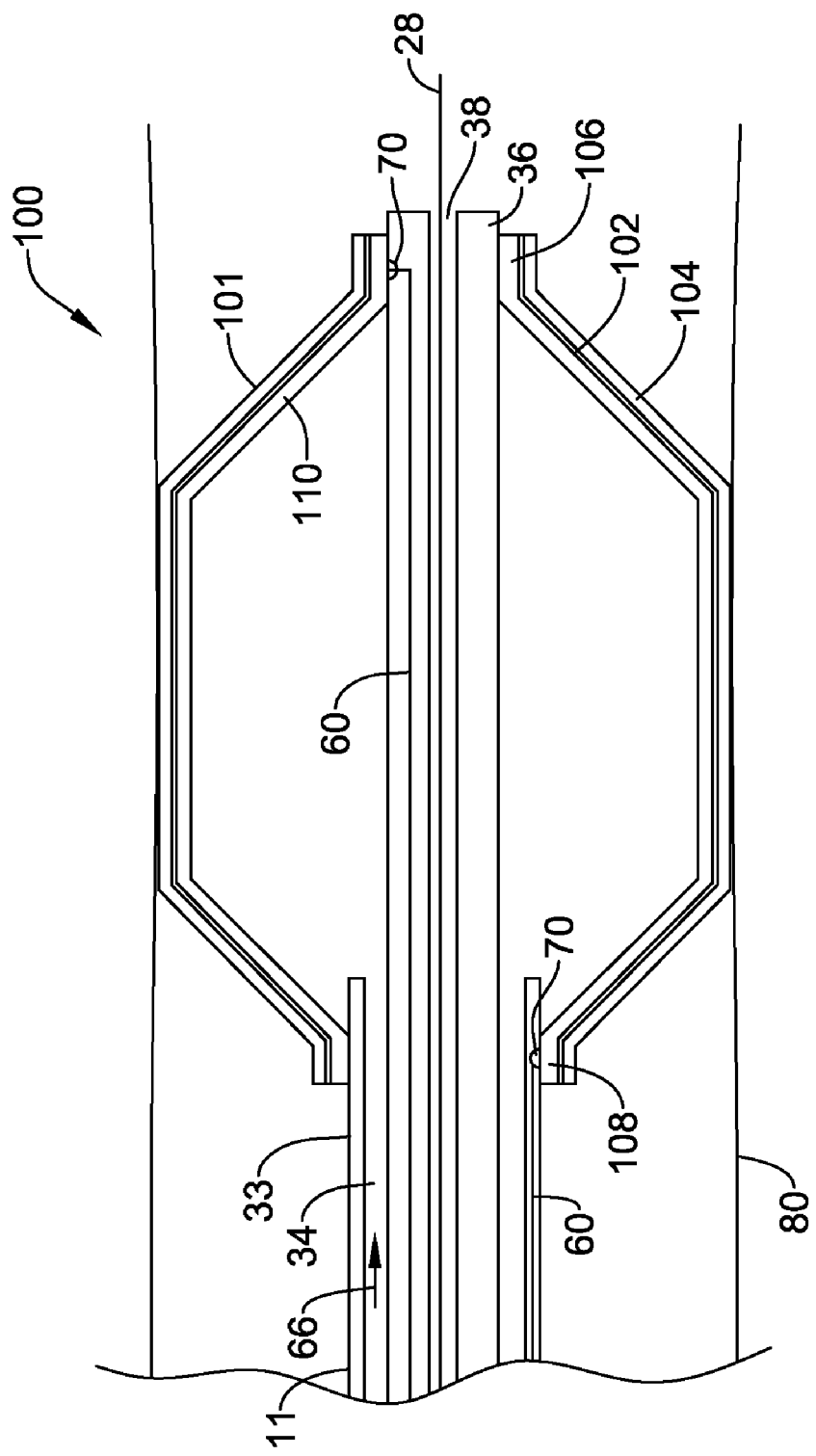
FIG. 9 is a longitudinal cross-sectional view of an illustrative embodiment of a catheter including a drug delivery balloon.

FIG. 9 is a longitudinal cross-sectional view of an illustrative embodiment of a catheter 100 including a drug delivery balloon 101 in a vessel 80. In the illustrative embodiment, drug delivery balloon 101 may be disposed about a portion of the elongated shaft 11. As illustrated, a proximal waist 108 of balloon 101 may be disposed about the outer shaft 33 of the elongated shaft 11 and a distal waist 106 of balloon may be disposed about the inner shaft 36 of the elongated shaft 11. As illustrated, the proximal waist 108 and the distal waist 106 may be fixed or otherwise secured to the outer shaft 33 and the inner shaft 36, respectively. However, it is contemplated that the proximal waist 108 and the distal waist 106 may be rotatably secured to the outer shaft 33 and the inner shaft 36, if desired.

In the illustrative embodiment, the drug delivery balloon 101 may include an inner inflatable balloon portion 110, a conductive plating 102 disposed about at least a portion of the inner balloon portion 110, and an EAP layer 104 disposed about at least a portion of the conductive plating 102. As illustrated, the conductive plating 102 is shown disposed about the entire inner balloon portion 110, however, it is contemplated that the conductive plating may be provided about only a portion of the inner balloon portion 110, in strips about the inner balloon portion 110, or in any other suitable location to provide an electrical current to activate the EAP layer 104, as desired.

Similar to catheter 10 described above, conductive wires 60 may be provided to electrically connect the EAP layer 104 and/or conductive layer 102 to the activation circuit. In the illustrative embodiment, it is contemplated that one of wires 60 may provide the current to the EAP layer 104 and/or conductive layer 102 and a second one of wires 60 may provide the return path to complete the circuit. Additionally, although not illustrated in FIG. 9, it is contemplated that one or more markers similar to those shown and described with reference to FIG. 3 may be provided with a wire to provide the return path for the current. Also, the fluid 66 may be utilized in the circuit, if desired.

In the illustrative embodiment, the EAP layer 104 may be loaded with drugs for releasing within vessel 80. Upon activation or deactivation of the EAP layer 104, the drugs may be released in to the vessel 80. Furthermore, it is contemplated that the activation circuit for activating EAP layer 104 may or may not include hysteresis, as desired. It is also contemplated that activation circuit 90 or activation 97 may be used to activate the EAP layer, as desired. It is also contemplated that instead of timer 98, shown in FIG. 8, circuit 97 may include an element (not shown) that measures the current that has been provided to the EAP layer. In one example, the element may measure the current in Coulombs. In this case, a second comparator (not shown) may be used to switch off the electrical supply to the collars 40 and 42 once a predefined or predetermined charge level has been reached and/or exceeded. In some cases, the charge may be directly correlated to the amount of drug molecules being expelled from the EAP layer and, as such, measuring the charge may provide a precise or accurate determination of the amount of drugs released.

Example drugs that may be released in the vessel 80 by the EAP layer 104 may include an anti-thrombogenic drug, such as heparin; low molecular weight heparin, e.g., ENOXAPRIN; aspirin; phe-L-pro-L-arginyl chloromethyl ketone (PPACK); hirudin, HIRULOG®; Warfarin; Argatroban; or tissue factor pathway inhibitor (TPFI). The drug may also be a thrombolytic drug, such as urokinase; pro-urokinase; streptokinase; tissue plasminogen activator; anisolated plasminogen streptokinase activator complex (APSAC), e.g., EMINASE®; an inhibitor of PAI-1, TA plasminogen; or cathepepsin D. Anti-platelet agents, such as chimeric 7E3 antibody (Reopro); Ticolpidine; Integrilin; TP9201; nitric oxide (NO) and derivatives thereof, e.g., protein-linked NO; Iloprost, or MK383, may be similarly delivered and triggered. Other drugs suitable for delivery in this manner include protein and polypeptide drugs, e.g., angiogenesis factors including but not limited to fibroblast growth factor (FGF), vascular endothelial growth factor (VEGF), transforming growth factor-beta, (TGF.beta.), platelet-derived growth factor (PDGF), epidermal growth factor (EGF), and urokinase. Other drugs to be delivered include those to treat benign hyperplasia, e.g., PROSCAR®, and HYTRIN®. Other drugs include antiproliferative drugs, such monoclonal antibodies capable of blocking smooth muscle cell proliferation, e.g., anti-PDGF and anti-FGF; tyrosine kinase inhibitors, e.g., tyrophosphins, antisense oligonucleotides to c-myc, c-myb; NO; gene encoding thymidine kinase (TK); fusion toxins, e.g., $DAB_{389}$-EGF; immunotoxins, angiopeptin; antioxidant drugs, e.g., probudol, lovastatin, vitamin C and vitamin E; calcium channel blockers, e.g., nificitine, veratimil, ACE inhibitors, fofinopril and cilazapril. Chemotherapeutic drugs to treat various forms of cancer, e.g., HLB-7; granulocyte macrophage colony stimulating factor (GM-CSF); interferon.gamma.; immunotoxins, e.g., BMS-18224801, and BR-96-DOX; ONCOLYSIN®; fusion toxins, e.g., $DAB_{389}$-IL-2, and $DAB_{389}$-EGF; 5-Fluorouracil; methotrexate; and TAXOL®. However, any suitable drug may be released by the EAP layer 104, as desired.

In at least some embodiments, portions or all of catheters 10 and/or 100, or other components that are part of or used in the device, may be doped with, made of, or otherwise include a radiopaque material. Radiopaque materials are understood to be materials capable of producing a relatively bright image on a fluoroscopy screen or another imaging technique during a medical procedure. This relatively bright image aids the user of devices 10 and/or 100 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may be incorporated into the design of catheters 10 and/or 100 to achieve the same result.

In some embodiments, a degree of MRI compatibility is imparted into catheters 10 and/or 100. For example, to enhance compatibility with Magnetic Resonance Imaging (MRI) machines, it may be desirable to make elongated shaft 11, inflatable balloon 14, and/or inflatable balloon 101, or other portions of the medical devices 10 and/or 100, in a manner that would impart a degree of MRI compatibility. For example, elongated shaft 11, inflatable balloon 14, and/or inflatable balloon 101, or portions thereof, may be made of a material that does not substantially distort the image and create substantial artifacts (artifacts are gaps in the image). Certain ferromagnetic materials, for example, may not be suitable because they may create artifacts in an MRI image. Elongated shaft 11, inflatable balloon 14, and/or inflatable balloon 101, or portions thereof, may also be made from a material that the MRI machine can image. Some materials that exhibit these characteristics include, for example, tungsten, Elgiloy, MP35N, nitinol, and the like, and others.

In some embodiments, a sheath and/or coating, for example a lubricious, a hydrophilic, a protective, or other type of material may be applied over portions or all of the elongated shaft 11, inflatable balloon 14, and/or inflatable balloon 101, or other portions of devices 10 and/or 100. Some examples of suitable polymer sheath materials may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

In some embodiments sheath material can be blended with a liquid crystal polymer (LCP). For example, the mixture can contain up to about 6% LCP. This has been found to enhance torqueability. By employing selection of materials and processing techniques, thermoplastic, solvent soluble, and thermosetting variants of these and other materials can be employed to achieve the desired results. Some examples of suitable coating materials may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof Some coating polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

A coating and/or sheath may be formed, for example, by coating, extrusion, co-extrusion, interrupted layer co-extrusion (ILC), or fusing several segments end-to-end. The layer may have a uniform stiffness or a gradual reduction in stiffness from the proximal end to the distal end thereof The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

In some cases, elongated shaft 11 can be made of the same material along its length, or in some embodiments, can include portions, sections, or layers made of different materials. In some embodiments, the material used to construct elongated shaft 11 are chosen to impart varying flexibility, torqueability, and stiffness characteristics to different portions of elongated shaft 11.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification. It should be understood that this disclosure is, in many respects, only illustrative. Changes may be made in details, particularly in matters of shape, size, and arrangement of steps without exceeding the scope of the invention. For example, although set forth with specific reference to catheters in some of the example embodiments shown in the Figures and discussed above, the invention may relate to virtually any medical device that may aid a user of the device in advancing a device in a vessel. For example, the invention may be applied to medical devices such as a guidewire, a balloon catheter, an atherectomy catheter, a drug delivery catheter, a stent delivery catheter, an endoscope, a fluid delivery device, other infusion or aspiration devices, delivery (i.e. implantation) devices, and the like. Thus, while the Figures and descriptions above are directed toward a catheter, in other applications, sizes in terms of diameter, width, and length may vary widely, depending upon the desired properties of a particular device. The scope of the invention is, of course, defined in the language in which the appended claims are expressed.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device comprising: an elongated member including a proximal end, a distal end, and a lumen extending therebetween; a balloon disposed about at least a portion of the elongated member adjacent to the distal end, wherein the balloon is fluidly connected to the lumen of the elongated member to receive a fluid for inflating the balloon; one or more electroactive polymers disposed adjacent to at least a portion of the balloon, wherein the one or more electroactive polymers are electrically actuatable between a first contracted state and a second expanded state; an activation circuit including a sensor for sensing a measure related to a parameter within the elongated member and/or balloon, wherein the activation circuit is coupled to the one or more electroactive polymers for selectively providing an electrical current to the one or more electroactive polymers according to the sensed measure; and wherein the activation circuit includes a comparator having a first input connected to the sensor and a second input connected to a predefined threshold value, wherein the sensed measure is compared to the predefined threshold value.

2. The medical device of claim 1 wherein the activation circuit provides the electrical current to the one or more electroactive polymers when the sensed measure is greater than the predefined threshold value.

3. The medical device of claim 1 wherein the predefined threshold value includes a turn on threshold value and a turn off threshold value, wherein the turn off threshold value is less than the turn on threshold value, wherein the activation circuit switches on the electrical current to the one or more electroactive polymers when the sensed characteristic of the fluid exceeds the turn on threshold value and the activation circuit switches off the electrical current to the one or more electroactive polymers when the sensed characteristic of the fluid falls below the turn off threshold value.

4. The medical device of claim 1 wherein the comparator includes an operational amplifier.

5. The medical device of claim 1 wherein the comparator is a Schmitt trigger.

6. The medical device of claim 1 wherein the parameter is a fluidic pressure in the lumen and/or the balloon.

7. The medical device of claim 1 wherein the parameter is a rate of fluid flow through the lumen and/or the balloon.

8. The medical device of claim 1 wherein the parameter is a temperature in the lumen and/or the balloon.

9. The medical device of claim 1 wherein the activation circuit includes a mechanism for switching the electrical current on and off to the one or more electroactive polymers according to the sensed measure.

10. The medical device of claim 1 wherein the balloon includes a proximal waist and a distal waist disposed about the elongated member, and wherein the one or more electroactive polymers are disposed between the proximal waist and the elongated member and/or distal waist and the elongated member.

11. The medical device of claim 10 wherein when the one or more electroactive polymers are in the contracted state, the balloon is rotatable, and when the one or more electroactive polymers are in the expanded state, the balloon is non-rotatable.

12. The medical device of claim 1 wherein the balloon is a drug delivery balloon and the one or more electroactive polymers are disposed about at least a portion of the balloon, wherein when the one or more electroactive polymers are in the expanded state, one or more drugs are released from the balloon, and when the one or more electroactive polymers are in the contracted state, the one or more drugs are contained within the balloon.

13. The medical device of claim 1 wherein the activation circuit further includes a timer connected to the output of the comparator, wherein the timer is programmed to activate the one or more electroactive polymers for a period of time when the sensed characteristic of the fluid is greater than the threshold value.

14. The medical device of claim 1 wherein the activation circuit further includes a timer connected to the output of the comparator, wherein the timer is programmed to activate the one or more electroactive polymers at intervals of time when the sensed characteristic of the fluid is greater than the threshold value.

15. The medical device of claim 1 further comprising a stent disposed about at least a portion of the balloon.

16. A method of actuating an electroactive polymer between a contracted state and an expanded state in a medical device, the method comprising:
    providing an elongated member having a proximal end, a distal end, and a lumen extending therebetween;
    providing an inflatable balloon disposed about the elongated member adjacent to the distal end, wherein the balloon is fluidly coupled to the lumen;
    providing one or more electroactive polymers adjacent at least a portion of the balloon;
    providing an activation circuit including a sensor for sensing a measure related to a parameter within the elongated member and/or balloon, the activation circuit coupled to the one or more electroactive polymers;
    providing an inflation fluid through the lumen to inflate the balloon; and
    automatically actuating the electroactive polymer in response to providing the inflation fluid through the lumen, wherein automatically actuating the electroactive polymer includes:
        sensing a measure related to a parameter within the elongated member and/or balloon with the sensor;
        comparing the sensed measure to a first threshold; and
        providing a current to the electroactive polymer when the sensed measure is greater than the first threshold.

17. The method of claim 16 further comprising deactivating the electroactive polymer when the sensed characteristic is less than the first threshold.

18. The method of claim 16 further comprising:
    providing a second threshold that is less than the first threshold; and
    deactivating the electroactive polymer when the sensed measure is less than the second threshold.

19. The method of claim 16 wherein the parameter is a fluidic pressure in the lumen and/or the balloon.

20. The method of claim 16 wherein the parameter is a rate of fluid flow through the lumen and/or the balloon.

21. The method of claim 16 wherein the parameter is a temperature in the lumen and/or the balloon.

22. The method of claim 16 further comprising:
    counting the period of time that the electroactive polymer is activated; and
    deactivating the electroactive polymer if the period of time exceeds a time limit.

* * * * *

UNITED STATES PATENT AND TRADEMARK OFFICE
CERTIFICATE OF CORRECTION

PATENT NO. : 8,133,199 B2  
APPLICATION NO. : 12/199720  
DATED : March 13, 2012  
INVENTOR(S) : Jan Weber et al.

Page 1 of 1

It is certified that error appears in the above-identified patent and that said Letters Patent is hereby corrected as shown below:

Column 16  
Line 45: Delete "claim 1" and insert therefor -- claim 4 --.

Signed and Sealed this  
Twelfth Day of June, 2012

David J. Kappos  
*Director of the United States Patent and Trademark Office*